United States Patent
Kiyoshige

(10) Patent No.: US 10,687,734 B2
(45) Date of Patent: Jun. 23, 2020

(54) SERVER, CLIENT, COMMUNICATION SYSTEM, COMMUNICATION METHOD, AND RECORDING MEDIUM

(71) Applicant: OLYMPUS CORPORATION, Hachioji-shi, Tokyo (JP)

(72) Inventor: Ryuichi Kiyoshige, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 35 days.

(21) Appl. No.: 15/964,421

(22) Filed: Apr. 27, 2018

(65) Prior Publication Data
US 2018/0242882 A1 Aug. 30, 2018

Related U.S. Application Data

(63) Continuation of application No. PCT/JP2015/081870, filed on Nov. 12, 2015.

(51) Int. Cl.
*G06F 15/16* (2006.01)
*A61B 5/07* (2006.01)
(Continued)

(52) U.S. Cl.
CPC ............ *A61B 5/07* (2013.01); *A61B 1/00059* (2013.01); *A61B 1/273* (2013.01);
(Continued)

(58) Field of Classification Search
CPC . A61B 1/00059; A61B 1/273; A61B 5/02042; A61B 5/07; A61B 5/4887;
(Continued)

(56) References Cited

U.S. PATENT DOCUMENTS 9,715,939 B2* 7/2017 Ellis .................. G11C 16/10
9,753,649 B2* 9/2017 Prins .................. G06F 11/1441
(Continued)

FOREIGN PATENT DOCUMENTS

JP 2009-44686 A 2/2009
JP 2009-111562 A 5/2009

OTHER PUBLICATIONS

International Search Report dated Jan. 26, 2016, issued in counterpart International Application No. PCT/JP2015/081870, w/English translation (2 pages).
(Continued)

*Primary Examiner* — Liang Che A Wang
(74) *Attorney, Agent, or Firm* — Westerman, Hattori, Daniels & Adrian, LLP

(57) ABSTRACT

A server has a communicator, a decision unit, and a communication control unit. In a case in which a first condition and a second condition are satisfied, the decision unit decides to cause a first client to stop data transmission. In a case in which the first condition and a third condition are satisfied, the decision unit decides to cause a second client to stand by for the data transmission. The first condition indicates that an access point to which the first client is being connected is the same as an access point to which the second client is being connected. The second condition indicates that a priority of the first client is lower than a priority of the second client. The third condition indicates that priority information has not been received from the second client.

9 Claims, 13 Drawing Sheets

(51) Int. Cl.

| | | |
|---|---|---|
| *H04L 12/28* | (2006.01) | |
| *A61B 1/00* | (2006.01) | |
| *A61B 1/273* | (2006.01) | |
| *H04W 28/02* | (2009.01) | |
| *A61B 5/00* | (2006.01) | |
| *H04L 12/825* | (2013.01) | |
| *A61B 5/02* | (2006.01) | |
| *H04W 74/00* | (2009.01) | |
| *G16H 30/40* | (2018.01) | |
| *G16H 20/40* | (2018.01) | |
| *H04W 76/28* | (2018.01) | |
| *G16H 40/67* | (2018.01) | |
| *H04W 28/16* | (2009.01) | |
| *H04W 84/12* | (2009.01) | |

(52) U.S. Cl.
CPC ........ *A61B 5/02042* (2013.01); *A61B 5/4887* (2013.01); *G16H 20/40* (2018.01); *G16H 30/40* (2018.01); *G16H 40/67* (2018.01); *H04L 12/28* (2013.01); *H04L 47/266* (2013.01); *H04W 28/02* (2013.01); *H04W 28/16* (2013.01); *H04W 74/00* (2013.01); *H04W 76/28* (2018.02); *H04W 84/12* (2013.01); *Y02D 70/00* (2018.01); *Y02D 70/142* (2018.01)

(58) Field of Classification Search
CPC ........ G16H 20/40; G16H 30/40; G16H 40/67; H04L 12/28; H04L 47/266; H04W 28/02; H04W 28/16; H04W 74/00; H04W 76/28; H04W 84/12; Y02D 70/00; Y02D 70/142
USPC .......... 709/203, 217, 218, 219, 226
See application file for complete search history.

(56) References Cited

U.S. PATENT DOCUMENTS

| | | | | |
|---|---|---|---|---|
| 9,778,878 | B2 * | 10/2017 | Hodgdon | ............... G06F 3/061 |
| 9,817,752 | B2 * | 11/2017 | Desai | ................. G06F 12/0246 |
| 9,824,007 | B2 * | 11/2017 | Desai | ................. G06F 12/0246 |
| 9,870,149 | B2 * | 1/2018 | Sprouse | ............... G06F 3/0604 |
| 9,952,978 | B2 * | 4/2018 | Sprouse | ............. G06F 12/0868 |
| 2015/0067172 | A1 * | 3/2015 | Ashokan | ............... H04L 47/743 709/226 |
| 2015/0229050 | A1 * | 8/2015 | Shimoji | ............. H01R 12/7082 439/81 |
| 2019/0068519 | A1 * | 2/2019 | Laird | ................... H04L 47/748 |

OTHER PUBLICATIONS

Notice of Allowance dated Mar. 26, 2019, issued in counterpart JP application No. 2017-549939, with English translation. (6 pages).

* cited by examiner

SERVER, CLIENT, COMMUNICATION SYSTEM, COMMUNICATION METHOD, AND RECORDING MEDIUM

The present application is a continuation application based on International Patent Application No. PCT/JP 2015-081870, filed Nov. 12, 2015, the content of which is incorporated herein by reference.

BACKGROUND OF THE INVENTION

Field of the Invention

The present invention relates to a server, a client, a communication system, a communication method, and a recording medium.

Description of Related Art

Client server systems that include a wireless endoscope and a capsule endoscope have been created. In these systems, an examination-and-analysis device and an examination-and-treatment device are separate. The examination-and-analysis device analyzes examination data received from the examination-and-treatment device and provides a visual notification of examination results to a user. The examination-and-treatment device transmits the examination data received from an external terminal in a body to the examination-and-analysis device. The examination-and-analysis device and the examination-and-treatment device are connected to a network and communicate data.

This system has one examination-and-analysis device and a plurality of examination-and-treatment devices. For a small-intestine examination using a capsule endoscope, it takes a long time to conduct the examination. Therefore, a patient to which the examination-and-treatment device is attached is allowed to have freedom of action to some extent. The examination-and-treatment devices are driven by batteries in order to enable wireless communication and moving. Meanwhile, the examination-and-analysis device is installed at a location at which a doctor can check the examination results as needed. That is, the examination-and-analysis device and the examination-and-treatment devices are disposed at mutually separate locations. A network infrastructure in a hospital is utilized for the examination-and-treatment device to transmit the acquired examination data to the examination-and-analysis device.

A wireless network infrastructure may have a problem regarding communication traffic. In a case in which the examination-and-treatment devices can communicate a predetermined amount of data at a high communication speed, data transmission is completed in a short time. Power consumed by the examination-and-treatment devices can be saved by stopping a communication function in the examination-and-treatment devices after data transmission is completed. Meanwhile, in a case in which a plurality of examination-and-treatment devices freely perform data communication, the plurality of examination-and-treatment devices compete for a limited communication band. Therefore, communication traffic increases, and communication speeds becomes lower as a whole. As a result, the respective examination-and-treatment devices are not be able to end data transmission in a short time and continue communication. This leads to an increase in power consumption.

According to Japanese Unexamined Patent Application, First Publication No. 2009-111562, a server extracts information related to a wireless LAN access point (relay device included in a signal received from a client. The server measures the amount of communication data for each relay device and adds communication amount information of the relay device to transmission data. The server transmits the transmission data, to which the communication amount information has been added, to the client. The client acquires identification information of the relay device used. The client extracts the communication amount information of the relay device included in the data received from the server. The client sets a waiting time on the basis of the communication amount information. The client performs communication after waiting for the waiting time. According to the technology disclosed in Japanese Unexamined Patent Application, First Publication No. 2009-111562, the server and the client can efficiently perform communication while avoiding unnecessary traffic due to congestion when the usage rate of the network increases.

SUMMARY OF THE INVENTION

According to a first aspect of the present invention, a server has a communicator, a decision unit, and a communication control unit. The communicator receives data at an application level from a client and receives connection AP information and priority information from the client before reception of the data is started. The client is one of a first client and a second client. The first client is a terminal that has already started data transmission to the server at a timing when decision processing is started. The second client is a terminal that is standing by for the data transmission to the server at the timing when the decision processing is started. The connection AP information indicates an access point to which the client is being connected. The priority information indicates a priority of the client. The decision unit determines whether or not a first condition is satisfied and determines whether or not any one of a second condition and a third condition is satisfied in the decision processing. The decision unit decides to cause the first client to stop data transmission in the decision processing in a case in which the first condition and the second condition are satisfied. The decision unit decides to cause the second client to stand by for the data transmission in the decision processing in a case in which the first condition and the third condition are satisfied. The first condition indicates that an access point indicated by the connection AP information received from the first client is the same as an access point indicated by the connection AP information received from the second client. The second condition indicates that a priority indicated by the priority information received from the first client is lower than a priority indicated by the priority information received from the second client. The third condition indicates that the priority information has not been received from the second client. The communication control unit transmits first control information to the first client by using the communicator in a case in which the decision unit decides to cause the first client to stop the data transmission. The communication control unit transmits second control information to the second client by using the communicator in a case in which the decision unit decides to cause the second client to stand by for the data transmission. The first control information indicates an instruction to stop data transmission via an access point to which the first client is being connected. The second control information indicates an instruction to stand by for data transmission via an access point to which the second client is being connected.

According to a second aspect of the present invention, in the first aspect, the communicator may further receive surrounding AP information from the client before the reception of the data is started. The surrounding AP information indicates an access point, to which the client is not being connected, which is present in surroundings of the client. The communication control unit may further transmit connection instruction information to the second client by using the communicator in a case in which the first condition is satisfied and the surrounding AP information has been received. The connection instruction information indicates an instruction to connect to the access point indicated by the surrounding AP information.

According to a third aspect of the present invention, in the first aspect, the communication control unit may further transmit clock time information to the first client by using the communicator in a case in which the decision unit decides to cause the first client to stop the data transmission. The communication control unit may further transmit the clock time information to the second client by using the communicator in a case in which the decision unit decides to cause the second client to stand by for the data transmission. The clock time information indicates a clock time when data transmission via an access point to which the first client or the second client is being connected may be started.

According to a fourth aspect of the present invention, in the third aspect, the communicator may further receive data amount information from the client before the reception of the data is started. The data amount information indicates the amount of data that is scheduled to be transmitted to the server. The decision unit may calculate the clock time on the basis of a first data amount and a second data amount in a case in which the decision unit decides to cause the first client to stop the data transmission. The first data amount is the amount of data indicated by the data amount information received from the first client. The second data amount is the amount of data that has already been received from the first client. The decision unit may calculate the clock time on the basis of the amount of data indicated by the data amount information received from the second client in a case in which the decision unit decides to cause the second client to stand by for the data transmission.

According to a fifth aspect of the present invention, in the first aspect, the data may be examination data that is acquired by an examination terminal for examining the inside of a body. The priority information may be at least one of position information, abnormality information, and operation information. The position information indicates a position of the examination terminal in the body. The abnormality information indicates a degree of abnormality of the inside of the body estimated from the examination data. The operation information indicates occurrence of a predetermined operation by a user.

According to a sixth aspect of the present invention, in the first aspect, the decision unit may further determine whether or not data transmission by a transmitting client will end within a predetermined time on the basis of a data transmission ability of the transmitting client after one of the first control information and the second control information is transmitted. The transmitting client is the second client in a case in which the first control information is transmitted. The transmitting client is the first client in a case in which the second control information is transmitted. The decision unit may further decide to cause the transmitting client to stop the data transmission in a case in which the data transmission by the transmitting client will not end within the predetermined time. The communication control unit may further transmit third control information to the transmitting client by using the communicator in a case in which the decision unit decides to cause the transmitting client to stop the data transmission. The third control information indicates an instruction to stop data transmission via an access point to which the transmitting client is being connected.

According to a seventh aspect of the present invention, a client is one of a first client and a second client. The first client is a terminal that has already started data transmission to a server at a timing when decision processing is started. The second client is a terminal that is standing by for the data transmission to the server at the timing when the decision processing is started. The decision processing is processing for deciding which of a first state and a second state to be set. The first state is a state in which the first client performs data transmission. The second state is a state in which the second client performs data transmission. The client has a communicator and a communication control unit. The communicator receives data at an application level from an external terminal. The communicator transmits the data received from the external terminal to the server. The communicator transmits connection AP information, priority information, and surrounding AP information to the server before transmission of the data is started. The communicator receives one of first control information, second control information, and connection instruction information from the server. The connection AP information indicates an access point to which the client is being connected. The priority information indicates a priority of the client. The surrounding AP information indicates an access point to which the client is not being connected, which is present in surroundings of the client. The first control information indicates an instruction to stop data transmission via an access point to which the first client is being connected. The second control information indicates an instruction to stand by for data transmission via an access point to which the second client is being connected. The connection instruction information indicates an instruction to connect to the access point indicated by the surrounding AP information. The communication control unit stops the data transmission via the access point to which the first client is being connected in a case in which the first control information has been received. The communication control unit stands by for the data transmission via the access point to which the second client is being connected in a case in which the second control information has been received. The communication control unit connects to the access point indicated by the surrounding AP information by using the communicator in a case in which the connection instruction information has been received.

According to an eighth aspect of the present invention, in the seventh aspect, the communicator may further receive clock time information from the server. The clock time information indicates a clock time when data transmission via an access point to which the first client or the second client is being connected may be started. The communication control unit may further start the data transmission via the access point to which the first client or the second client is being connected at the clock time indicated by the clock time information in a case in which one of the first control information and the second control information has been received and the clock time information has been received.

According to a ninth aspect of the present invention, in the seventh aspect, the communicator may further transmit data amount information to the server before the transmission of the data is started. The data amount information indicates the amount of data that is scheduled to be transmitted to the server.

According to a tenth aspect of the present invention, in the seventh aspect, the external terminal may be an examination terminal for examining the inside of a body. The data may be examination data acquired by the examination terminal. The priority information may be at least one of position information, abnormality information, and operation information. The position information indicates a position of the examination terminal in the body. The abnormality information indicates a degree of abnormality of the inside of the body estimated from the examination data. The operation information indicates occurrence of a predetermined operation by a user.

According to an eleventh aspect of the present invention, in the tenth aspect, the client may further have an examination data processing unit that generates the position information and the abnormality information on a basis of the examination data.

According to a twelfth aspect of the present invention, in the seventh aspect, the client may further have a data processing unit that reduces the amount of the data transmitted to the server in a case in which a battery remaining amount of the client is less than a predetermined amount. The communication control unit may transmit the data, the amount of which has been reduced, to the server by using the communicator.

According to a thirteenth aspect of the present invention, in the seventh aspect, the communicator may include a first communicator that communicates with the external terminal and a second communicator that communicates with the server. The client may further have a state control unit that brings only the second communicator into a resting state in a case in which a battery remaining amount of the client is less than a predetermined amount.

According to a fourteenth aspect of the present invention, a communication system has a server and a client. The server includes a first communicator, a decision unit, and a first communication control unit. The first communicator receives data at an application level from the client and receives connection AP information and priority information from the client before reception of the data is started. The client is one of a first client and a second client. The first client is a terminal that has already started data transmission to the server at a timing when decision processing is started. The second client is a terminal that is standing by for the data transmission to the server at the timing when the decision processing is started. The connection AP information indicates an access point to which the client is being connected. The priority information indicates a priority of the client. The decision unit determines whether or not a first condition is satisfied and determines whether or not any one of a second condition and a third condition is satisfied in the decision processing. The decision unit decides to cause the first client to stop the data transmission in the decision processing in a case in which the first condition and the second condition are satisfied. The decision unit decides to cause the second client to stand by for the data transmission in the decision processing in a case in which the first condition and the third condition are satisfied. The first condition indicates that an access point indicated by the connection AP information received from the first client is the same as an access point indicated by the connection AP information received from the second client. The second condition indicates that a priority indicated by the priority information received front the first client is lower than a priority indicated by the priority information received from the second client. The third condition indicates that the priority information has not been received from the second client. The first communication control unit transmits first control information to the first client by using the first communicator in a case in which the decision unit decides to cause the first client to stop the data transmission. The first communication control unit transmits second control information to the second client by using the first communicator in a case in which the decision unit decides to cause the second client to stand by for the data transmission. The first control information indicates an instruction to stop data transmission via an access point to which the first client is being connected. The second control information indicates an instruction to stand by for the data transmission via the access point to which the second client is being connected. The client has a second communicator and a second communication control unit. The second communicator receives the data from an external terminal. The second communicator transmits the data received from the external terminal to the server. The second communicator transmits the connection AP information and the priority information to the server before transmission of the data is started. The second communicator receives one of the first control information and the second control information from the server. The second communication control unit stops the data transmission via the access point to which the first client is being connected in a case in which the first control information has been received. The second communication control unit stands by for the data transmission via the access point to which the second client is being connected in a case in which the second control information has been received.

According to a fifteenth aspect of the present invention, a communication method that is performed by a server has a first step, a second step, a third step, and a fourth step. The server receives data at an application level from a client in the first step. The client is one of a first client and a second client. The first client is a terminal that has already started data transmission to the server at a timing when decision processing is started. The second client is a terminal that is standing by for the data transmission to the server at the timing when the decision processing is started. The server receives connection AP information and priority information from the client in the second step before reception of the data is started. The connection AP information indicates an access point to which the client is being connected. The priority information indicates a priority of the client. The server determines whether or not a first condition is satisfied and determines whether or not any one of a second condition and a third condition is satisfied in the decision processing in the third step. The server decides to cause the first client to stop the data transmission in the decision processing in a case in which the first condition and the second condition are satisfied. The server decides to cause the second client to stand by for the data transmission in the decision processing in the third step in a case in which the first condition and the third condition are satisfied. The first condition indicates that an access point indicated by the connection AP information received from the first client is the same as an access point indicated by the connection AP information received from the second client. The second condition indicates that a priority indicated by the priority information received from the first client is lower than a priority indicated by the priority information received from the second client. The third condition indicates that the priority information has not been received from the second client. The server transmits first control information to the first client in the fourth step in a case in which the server decides to cause the first client to stop the data transmission in the third step. The server transmits second control information to the second client in the fourth step in a case in which the server decides to cause the second client to stand by for the data transmission in the third step. The first control information indicates an instruction to stop data transmission via an access point to which the first client is being connected. The second control information indicates an instruction to stand by for data transmission via an access point to which the second client is being connected.

According to a sixteenth aspect of the present invention, a communication method that is performed by a client has a first step, a second step, a third step, a fourth step, and a fifth step. The client is one of a first client and a second client. The first client is a terminal that has already started data transmission to a server at a timing when decision processing is started. The second client is a terminal that is standing by for the data transmission to the server at the timing when the decision processing is started. The decision processing is processing for deciding which of a first state and a second state to be set. The first state is a state in which the first client performs data transmission. The second state is a state in which the second client performs data transmission. The client receives data at an application level from an external terminal in the first step. The client transmits the data received from the external terminal to the server in the second step. The client transmits connection AP information, priority information, and surrounding AP information to the server in the third step before transmission of the data is started. The connection AP information indicates an access point to which the client is being connected. The priority information indicates a priority of the client. The surrounding AP information indicates an access point, to which the client is not being connected, which is present in surroundings of the client. The client receives one of first control information, second control information, and connection instruction information from the server in the fourth step. The first control information indicates an instruction to stop data transmission via an access point to which the first client is being connected. The second control information indicates an instruction to stand by for data transmission in an access point to which the second client is being connected. The connection instruction information indicates an instruction to connect to the access point indicated by the surrounding AP information. The client stops the data transmission via the access point to which the first client is being connected in the fifth step in a case in which the first control information has been received. The client stands by for the data transmission via the access point to which the second client is being connected in the fifth step in a case in which the second control information has been received. The client connects to the access point indicated by the surrounding AP information in the fifth step a case in which the connection instruction information has been received.

According to a seventeenth aspect of the present invention, a non-transitory computer-readable recording medium is provided that records a program for causing a computer of a server to execute a first step, a second step, a third step, and a fourth step. The server receives data at an application level from a client in the first step. The client is one of a first client and a second client. The first client is a terminal that has already started data transmission to the server at a timing when decision processing is started. The second client is a terminal that is standing by for the data transmission to the server at the timing when the decision processing is started. The server receives connection AP information and priority information from the client in the second step before reception of the data is started. The connection AP information indicates an access point to which the client is being connected. The priority information indicates a priority of the client. The server determines whether or not a first condition is satisfied and determines whether or not any one of a second condition and a third condition is satisfied in the decision processing in the third step. The server decides to cause the first client to stop the data transmission in the decision processing in the third step in a case in which the first condition and the second condition are satisfied. The server decides to cause the second client to stand by for the data transmission in the decision processing in the third step in a case in which the first condition and the third condition are satisfied. The first condition indicates that an access point indicated by the connection AP information received from the first client is the same as an access point indicated by the connection AP information received from the second client. The second condition indicates that a priority indicated by the priority information received from the first client is lower than a priority indicated by the priority information received from the second client. The third condition indicates that the priority information has not been received from the second client. The server transmits first control information to the first client in the fourth step in a case in which the server decides to cause the first client to stop the data transmission in the third step. The server transmits second control information to the second client in the fourth step in a case in which the server decides to cause the second client to stand by for the data transmission in the third step. The first control information indicates an instruction to stop data transmission via an access point to which the first client is being connected. The second control information indicates an instruction to stand by for data transmission via an access point to which the second client is being connected.

According to an eighteenth aspect of the present invention, a non-transitory computer-readable recording medium is provided that records a program for causing a computer of a client to execute a first step, a second step a third step, a fourth step, and a fifth step. The client is one of a first client and a second client. The first client is a terminal that has already started data transmission to a server at a timing when decision processing is started. The second client is a terminal that is standing by for the data transmission to the server at the timing when the decision processing is started. The decision processing is processing for deciding which of a first state and a second state to be set. The first state is a state in which the first client performs data transmission. The second state is a state in which the second client performs data transmission. The client receives data at an application level from an external terminal in the first step. The client transmits the data received from the external terminal to the server in the second step. The client transmits connection AP information, priority information, and surrounding AP information to the server in the third step before transmission of the data is started. The connection AP information indicates an access point to which the client is being connected. The priority information indicates a priority of the client. The surrounding AP information indicates an access point, to which the client is not being connected, which is present in surroundings of the client. The client receives one of first control information, second control information, and connection instruction information from the server in the fourth step. The first control information indicates an instruction to stop data transmission via an access point to which the first client is being connected. The second control information indicates an instruction to stand by for data transmission via an access point to which the second client is being connected. The connection instruction information indicates an instruction to connect to the access point indicated by the surrounding AP information. The client stops the data transmission via the access point to which the first client is being connected in the fifth step in a case in which the first control information has been received. The client stands by for the data transmission via the access point to which the second client is being connected in the fifth step in a case in which the second control information has been received. The client connects to the access point indicated by the surrounding AP information in the fifth step in a case in which the connection instruction information has been received.

DETAILED DESCRIPTION OF THE INVENTION

An embodiment of the present invention will be described with reference to the drawings.

(Network Configuration)

Figure 1:
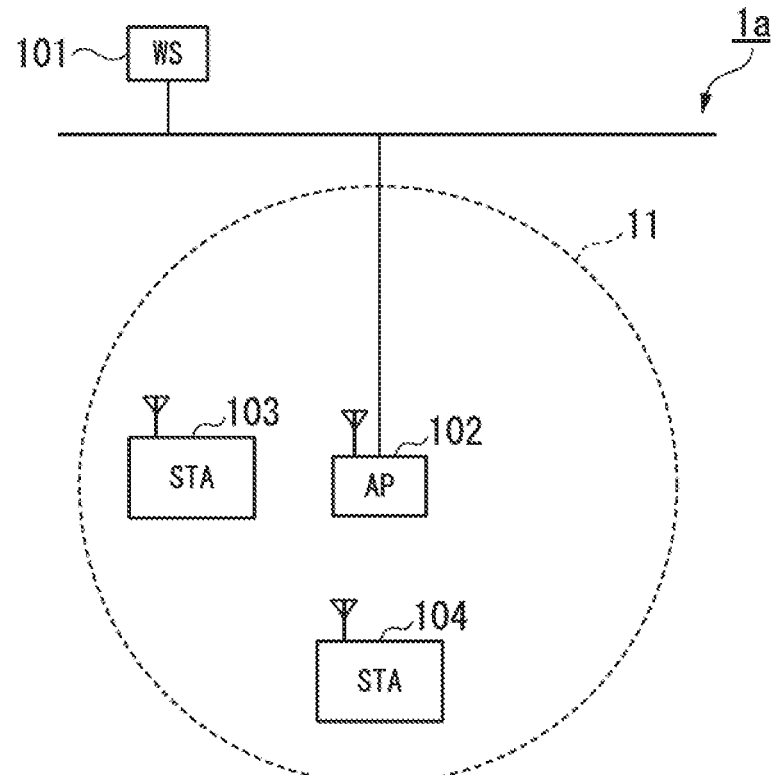
FIG. 1 is a configuration diagram of a network according to an embodiment of the present invention.
Figure 2:
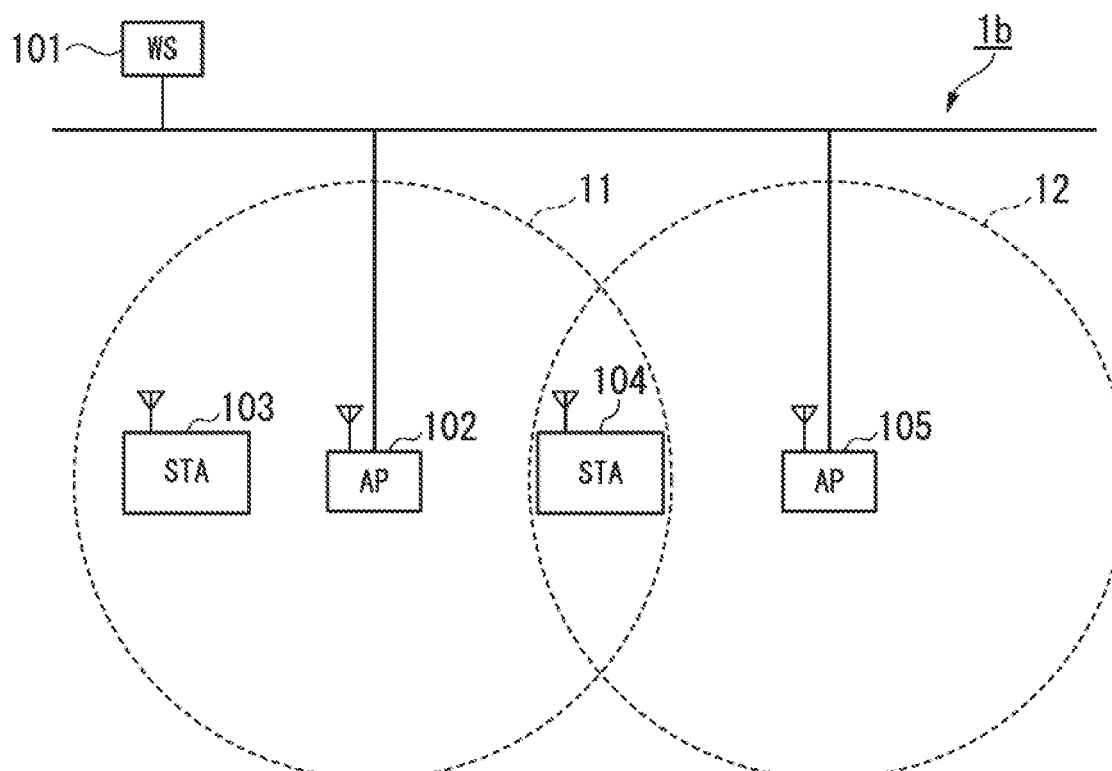
FIG. 2 is a configuration diagram of the network according to the embodiment of the present invention.
Figure 3:
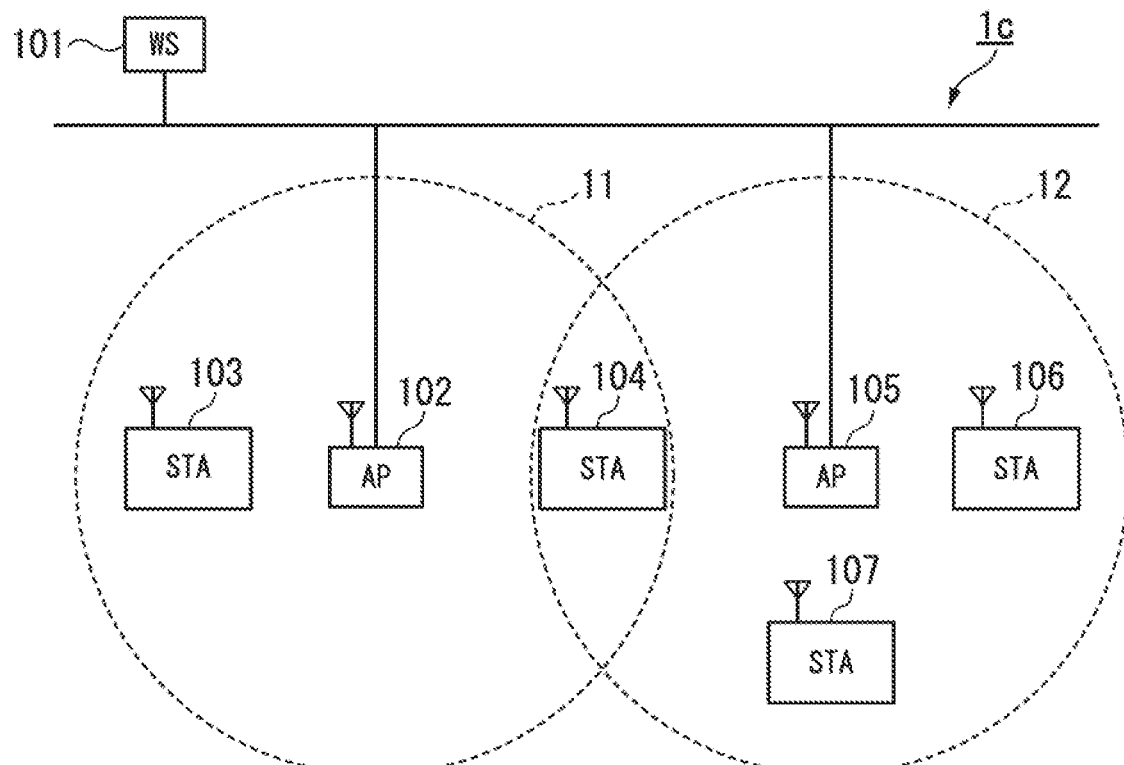
FIG. 3 is a configuration diagram of the network according to the embodiment of the present invention.

FIGS. 1 to 3 show a network configuration according to an embodiment of the present invention. FIG. 1 shows a configuration of a basic network 1a (communication system). As shown in FIG. 1, the network 1a has a WS 101 (server), an AP 102 (access point), an STA 103 (client), and an STA 104 (client). The WS 101 is an examination-and-analysis device. The AP 102 is a wireless access point. The WS 101 and the AP 102 form a wired network. Radio waves of the AP 102 reach a circular radio wave coverage range 11 around the AP 102 at the center. The STA 103 and the STA 104 are present inside the radio wave coverage range 11. The STA 103 and the STA 104 are examination-and-treatment devices. The STA 103 and the STA 104 perform wireless communication with the AP 102. Further, the STA 103 and the STA 104 perform wireless communication with an external terminal, which is not shown in the drawing, and receive data from the external terminal. The external terminal may be an examination terminal that performs examination of the inside of a body, for example. In FIG. 1, only two clients, namely, the STA 103 and the STA 104 are shown for convenience. A plurality of STAs may be present inside the radio wave coverage range 11 of the AP 102. The STA 103 and the STA 104 perform data communication with the WS 101 by using a communication path via the AP 102.

The data transmission assumed in the embodiment of the present invention is communication of data at an application level. For example, data communication in the application layer of the open systems interconnection (OSI) reference model is assumed.

The STA 103 and the STA 104 compete for a wireless network band via the AP 102 for transmitting data to the WS 101. In order to efficiently use the limited wireless network band, the WS 101 performs determination on the basis of information provided from each STA and provides an instruction to each STA. A determination method will be described later.

FIG. 2 shows a configuration of a network 1b (communication system). As shown in FIG. 2, the network 1b has a WS 101 (server), an AP 102 (access point), an STA 103 (client), an STA 104 (client), and an AP 105 (access point). The network 1b shown in FIG. 2 has the AP 105 added to the configuration of the network 1a shown in FIG. 1. Radio waves of the AP 105 reach a radio wave coverage range 12. The AP 102 and the AP 105 are disposed such that the radio waves from the AP 102 and the radio waves from the AP 105 overlap each other. The STA 104 is present in a range in which the radio waves from the AP 102 and the radio waves from the AP 105 overlap each other. Therefore, the STA 104 can connect wirelessly to an arbitrary one of the AP 102 and the AP 105. This is a typical method of designing a wireless network for avoiding disconnection or the like at the time of roaming.

In a case in which a plurality of STAs are present in the same path in the network 1a shown in FIG. 1, data communication by one STA is permitted in consideration of communication efficiency. Data communication by the other STA is brought into a stand-by state. In the network 1b shown in FIG. 2, the STA 104 can select a communication path that is different from a communication path that the STA 103 uses. An STA that performs data transmission to the WS 101 is not present in the communication path via the AP 105. Therefore, the WS 101 provides an instruction to select a communication path that is different from the communication path that the STA 103 uses and perform data transmission to the STA 104 by using the selected communication path. Details thereof will be described later.

FIG. 3 shows a configuration of a network 1c (communication system). As shown in FIG. 3, the network 1c has a WS 101 (server), an AP 102 (access point), an STA 103 (client), an STA 104 (client), an AP 105 (access point), an STA 106 (client), and an STA 107 (client). In the network is shown in FIG. 3, the STA 106 and the STA 107 are present in a radio wave coverage range 12 of the AP 105. The STA 104 can connect to an arbitrary one of the AP 102 and the AP 105. The STA 106 and the STA 107 compete for a wireless network band via the AP 105 in a communication path via the AP 105. Meanwhile, only the STA 103 is present as an STA other than the STA 104 in a communication path via the AP 102. Therefore, the WS 101 provides an instruction to perform data communication by using the communication path via the AP 102 to the STA 104. In a case in which the STA 103 has already performed data communication with the WS 101, the WS 101 provides an instruction to the STA 103 and the STA 104 in accordance with a predetermined determination method. Details thereof will be described later.

The WS 101 decides operations of the STA 103 and the STA 104 by performing decision processing. In a case in which the STA 103 and the STA 104 connect to the WS 101 via the AP 102 as shown in FIG. 1 or FIG. 3, the WS 101 decides operations of the STA 103 and the STA 104 in accordance with priorities of the STA 103 and the STA 104. In a case in which the priority of the STA 104 is higher than the priority of the STA 103, for example, the WS 101 provides an instruction to stop the data transmission that is being executed to the STA 103. The STA 104 performs the data communication via the AP 102. In a case in which the priority of the STA 103 is higher than the priority of the STA 104, the WS 101 provides an instruction to stand by for the data transmission to the STA 104. The STA 103 continues the data communication. In a case in which the STA 104 can connect to the WS 101 via the AP 105 as shown in FIG. 2, the WS 101 provides an instruction to connect to the AP 105 to the STA 104. The STA 104 performs the data communication via the AP 105. The details of the decision processing will be described later.

(System Configuration of WS)

Figure 4:
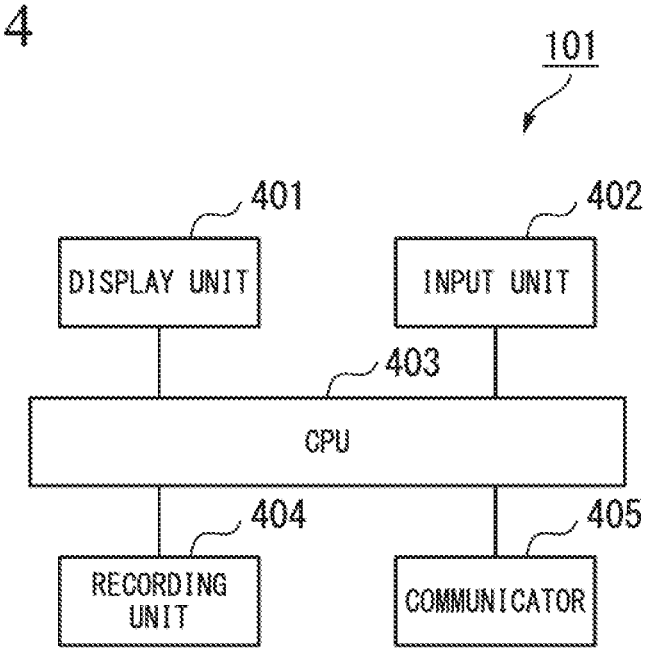
FIG. 4 is a block diagram showing a hardware configuration of a WS according to the embodiment of the present invention.

FIG. 4 shows a hardware configuration of the WS 101 (server) that is an examination-and-analysis device. As shown in FIG. 4, the WS 101 has a display unit 401, an input unit 402, a CPU 403, a recording unit 404, and a communicator 405.

The display unit 401 provides a visual notification of examination results generated by analyzing data received from the STA to a user. For example, the display unit 401 is a liquid crystal display. The input unit 402 receives an input operation from the user. For example, the input unit 402 is a keyboard. The CPU 403 controls the entire system of the WS 101 and executes a program for deciding an instruction for the STA on the basis of information received from the STA. Further, the CPU 403 executes a program for analyzing data received from the STA. The recording unit 404 is a recording medium for recording the data received from the STA and the examination results analyzed by the CPU 403. For example, the recording unit 404 is a hard disk. The communicator 405 performs data communication with the STA connected to a network to which the WS 101 is being connected. For example, the communicator 405 is a wired LAN adaptor. The communicator 405 may be a wireless LAN adaptor.

The communicator 405 receives connection AP information, priority information, surrounding AP information, and data amount information from the STA before reception of the data from the STA is started. The connection AP information indicates an access point to which the STA is being connected. The priority information indicates a priority of the STA. The priority information is at least one of position information, abnormality information, and operation information. The position information indicates the position of the examination terminal in the body. The abnormality information indicates a degree of abnormality of the inside of the body that is estimated from examination data generated by the examination terminal. The operation information indicates occurrence of a predetermined operation by the user. The surrounding AP information indicates an access point, to which the STA is not being connected, which is present in surroundings of the STA. That is, the surrounding AP information indicates an access point that is different from the access point, to which the STA is being connected, from among access points that are present in the surroundings of the STA. Each STA can connect to one access point. The data amount information indicates the amount of data that is scheduled to be transmitted to the WS 101. These information items are included in a transmission notification transmitted from the STA. The transmission notification indicates a request to start data transmission to the WS 101. The communicator 405 receives these information items from the STA by receiving the transmission notification from the STA. The STA, which has requested starting of the data transmission by the transmission notification, has not started data transmission to the WS 101. That is, the STA is waiting for the data transmission.

The communicator 405 transmits first control information, second control information, connection instruction information, clock time information, and third control information to the STA. The first control information indicates an instruction to stop the data transmission via the access point to which the STA transmitting the data is being connected. The second control information indicates an instruction to stand by for the data transmission via the access point to which the STA, which has not started the data transmission, is being connected. The connection instruction information indicates an instruction to connect to the access point indicated by the surrounding AP information. The connection instruction information may include information indicating the access point that is the same as the access point indicated by the surrounding AP information. The clock time information indicates a clock time when the data transmission via the access point to which the STA is being connected may be started. The third control information indicates an instruction to stop the data transmission via the access point to which the STA transmitting the data is being connected. These information items are included in an instruction notification transmitted from the WS 101. The communicator 405 transmits these information items to the STA by transmitting the instruction notification to the STA.

Figure 5:
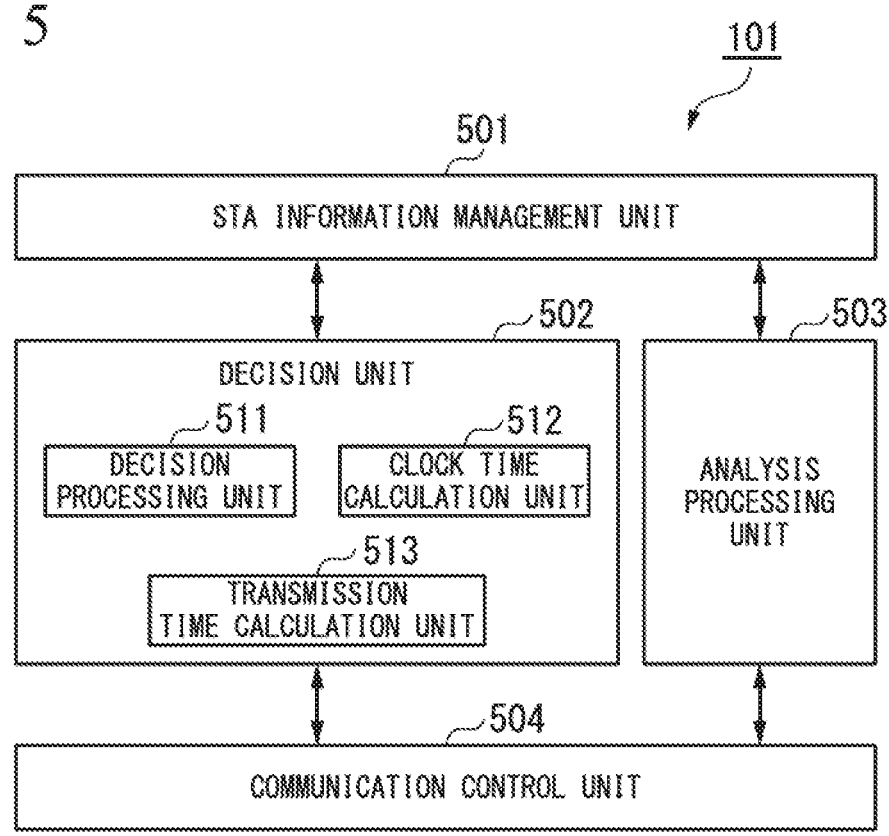
FIG. 5 is a block diagram showing a software configuration of the WS according to the embodiment of the present invention.

FIG. 5 shows a software configuration of the WS 101 (server) that is an examination-and-analysis device. Each component shown in FIG. 5 corresponds to a process generated by the CPU 403 executing a program. As shown in FIG. 5, the WS 101 has an STA information management unit 501, a decision unit 502, an analysis processing unit 503, and a communication control unit 504.

The STA information management unit 501 associates STA information provided from each STA with each STA and manages it. The STA information includes connection AP information, priority information, surrounding AP information, and data amount information.

The decision unit 502 has a decision processing unit 511, a clock time calculation unit 512, and a transmission time calculation unit 513. The decision processing unit 511 performs decision processing in a case in which a transmission notification has been received from the STA. The decision processing unit 511 determines which of a first client and a second client each STA is on the basis of the amount of data received from each STA in the decision processing. The first client is a terminal that has already started data transmission to the WS 101. In a case in which the amount of data received from an STA is greater than zero, the STA is the first client. The second client is a terminal that is standing by for data transmission to the WS 101. In a case in which the amount of data received from an STA is zero, the STA is the second client.

The decision processing unit 511 decides which of a first state and a second state to be set in the decision processing. The first state is a state in which the first client that is executing data communication transmits data. The second state is a state in which the second client that has requested to start data transmission by the transmission notification transmits data. In a case in which the decision processing unit 511 decides to cause the first client to stop the data transmission, the decision processing unit 511 generates first control information. In a case in which the decision processing unit 511 decides to cause the second client to stand by for the data transmission, the decision processing unit 511 generates second control information. The STA, which has received the first control information or the second control information is in a resting state with less power consumption than that in an ordinary state.

The decision processing unit 511 decides a connection destination of the second client on the basis of states of the other STAs in the decision processing. In a case in which the second client can connect to an access point that is different from an access point to which the first client is being connected, the decision processing unit 511 provides an instruction to connect to another access point to the second client. In a case in which the second client can connect to another access point, the decision processing unit 511 generates connection instruction information.

After one of the first control information and the second control information is transmitted, the decision processing unit 511 determines whether or not data transmission by an STA, which is transmitting the data, will end within a predetermined time on the basis of a data transmission ability of the STA. In a case in which the data transmission by the STA, which is transmitting the data, will not end within the predetermined time, the decision processing unit 511 decides to cause the STA to stop the data transmission and generates third control information. The third control information indicates an instruction to stop the data transmission via the access point to which the STA transmitting the data is being connected.

The clock time calculation unit 512 decides a clock time (wake-up clock time) at which an STA in the resting state will wake up. The wake-up clock time is a clock time when data transmission by the woken-up STA may be started. The STA in the resting state reverts to an ordinary state at the wake-up clock time. In a case in which the decision processing unit 511 decides to cause the first client executing the data transmission to stop the data transmission, the clock time calculation unit 512 calculates the wake-up clock time of the first client on the basis of a first data amount and a second data amount. The first data amount is the amount of data indicated by the data amount information received from the first client. The second data amount is the amount of data that has already been received from the first client. In a case in which the decision processing unit 511 decides to cause the second client, which has requested to start data transmission by a transmission notification, to stand by for data transmission, the clock time calculation unit 512 calculates a wake-up clock time of the second client on the basis of the amount of data indicated by data amount information received from the second client.

Specifically, the clock time calculation unit 512 measures a data transmission speed of the data transmission by the STA. In a case in which the decision processing unit 511 decides to cause the first client to stop the data transmission, the clock time calculation unit 512 calculates a length of time necessary for transmitting data, which has not yet been transmitted, on the basis of the first data amount, the second data amount, and the data transmission speed. For example, the clock time calculation unit 512 may subtract the second data amount from the first data amount. The clock time calculation unit 512 calculates the length of time necessary for transmitting the data, which has not yet been transmitted, by dividing the calculated value by the data transmission speed. The clock time calculation unit 512 calculates the wake-up clock time of the first client by adding the calculated time to a current clock time.

In a case in which the decision processing unit 511 decides to cause the second client to stop the data transmission, the clock time calculation unit 512 calculates the length of time necessary for transmitting the data, which has not yet been transmitted, on the basis of the amount of data indicated by the data amount information received from the second client. For example, the clock time calculation unit 512 calculates the length of time necessary for transmitting the data, which has not yet been transmitted, by dividing the amount of data indicated by the data amount information by the data transmission speed. The clock time calculation unit 512 calculates the wake-up clock time of the second client by adding the calculated time to the current clock time.

The transmission time calculation unit 513 calculates a remaining time until receiving data of the amount indicated by the data amount information is to be completed while the STA is transmitting the data. A method of calculating this time is similar to the method of calculating the length of time necessary for transmitting the data, which has not yet been transmitted, by the clock time calculation unit 512.

The analysis processing unit 503 performs various kinds of processing. For example, the analysis processing unit 503 performs decoding to convert data into data in a predetermined format in order to edit and display the data received from the STA. The analysis processing unit 503 selects data when the user designates a location that the user desires to view by time or the like. The user can input the location that the user desires to view via the input unit 402. The analysis processing unit 503 adds a mark, a comment, or the like to the data input by the user via the input unit 402.

The communication control unit 504 receives data or information from the STA by using the communicator 405. Specifically, the communication control unit 504 causes the communicator 405 to receive the data or the information transmitted from the STA. In this manner, the communicator 405 receives the data or the information from the STA. The communication control unit 504 transmits the information to the STA by using the communicator 405. Specifically, the communication control unit 504 causes the communicator 405 to transmit information to the STA. In this manner, the communicator 405 transmits the information to the STA.

The communication control unit 504 receives a transmission notification from the STA by using the communicator 405. The communication control unit 504 extracts information from the received transmission notification. The information extracted from the transmission notification is output to the decision unit 502. The communication control unit 504 generates an instruction notification that includes one of first control information, second control information, connection instruction information, and third control information. The instruction notification may include clock time information. The communication control unit 504 transmits the instruction notification to the STA by using the communicator 405.

The functions shown in FIG. 5 are realized as software by the CPU 403 reading and executing a program that includes commands defining these functions. The program may be provided by a "computer-readable recording medium" such as a flash memory, for example. In addition, the aforementioned program may be transmitted to the WS 101 via a transmission medium or transmission waves in the transmission medium from a computer that has a storage device or the like that saves the program therein. The "transmission medium" for transmitting the program may be a medium that has a function of transmitting information, which includes a network (communication network) such as the Internet or a communication connection (communication line) such as a telephone line. In addition, the aforementioned program may realize a part of the aforementioned functions. Further, the aforementioned program may be a differential file (differential program) that can realize the aforementioned functions in combination with programs that have already been recorded in the computer.

The functions shown in FIG. 5 may be constituted as a processor. For example, the processor may be at least one of a CPU, a digital signal processor (DSP), and a graphics processing unit (GPU). The processor may be at least one of an application specific integrated circuit (ASIC) and a field-programmable gate array (FPGA). The functions shown in FIG. 5 may include one or a plurality of processors.

(Configuration of STA)

Figure 6:
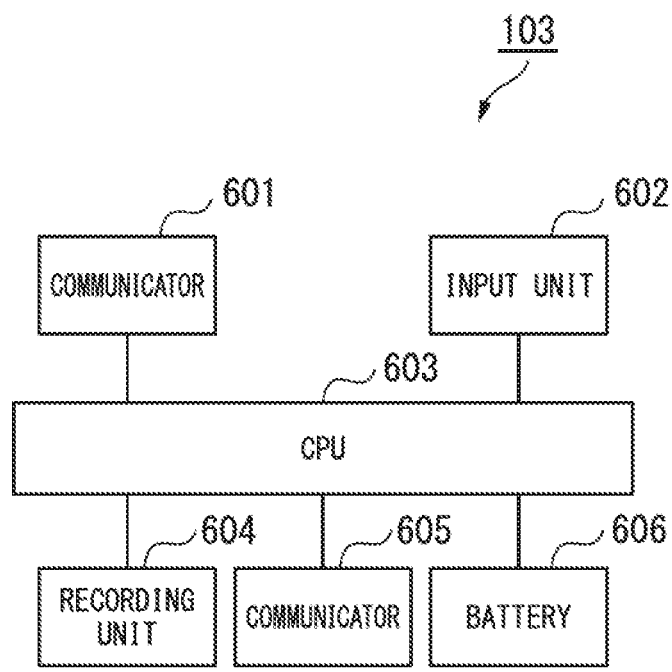
FIG. 6 is a block diagram showing a hardware configuration of an STA according to the embodiment of the present invention.

FIG. 6 shows a hardware configuration of an STA 103 (client) that is an examination-and-treatment device. Configurations of an STA 104, an STA 106, and an STA 107 are the same as the configuration of the STA 103. Therefore, only the configuration of the STA 103 will be described. As shown in FIG. 6, the STA 103 has a communicator 601, an input unit 602, a CPU 603, a recording unit 604, a communicator 605 and a battery 606.

The communicator 601 has an antenna and an integrated circuit (IC). The antenna of the communicator 601 transmits and receives radio waves. The IC of the communicator 601 performs base band processing and the like. The communicator 601 performs wireless communication with an access point in accordance with a predetermined communication protocol. In this manner, the communicator 601 performs communication with the WC 101. The communicator 601 may perform wired communication. The input unit 602 receives an input operation from the user. In a case in which the user intends to place priority on data transmission, for example, an instruction to perform data transmission with priority is input to the input unit 602.

The CPU 603 controls the entire system of the STA 103 and executes a program for processing examination data received from an external terminal. Further, the CPU 603 executes a program for managing various kinds of information provided to the WS 101 and generates a transmission notification to be transmitted to the WS 101. Further, the CPU 603 executes a program for analyzing an instruction notification received from the WS 101 and controlling a state of the STA 103 in accordance with the instruction notification.

The recording unit 604 is a recording medium that saves the examination data received from the external terminal. The communicator 605 has an antenna and an IC. The antenna of the communicator 605 transmits and receives radio waves. The antenna of the communicator 605 is compatible with a frequency band that is different from a frequency band with which the antenna of the communicator 601 is compatible. The IC of the communicator 605 performs base band processing and the like. The communicator 605 performs wireless communication with the external terminal in accordance with a predetermined communication protocol. In this manner, the communicator 605 receives the examination data from the external terminal. The communication protocol that the communicator 605 handles is a wireless protocol of a scheme that is different from that of a communication protocol that the communicator 601 handles. The battery 606 supplies electric power to the STA 103. The battery 606 is incorporated in the STA 103. Alternatively, the battery 606 can be removed from the STA 103.

The communicator 601 transmits data received from the external terminal to the WS 101. The communicator 601 transmits connection AP information, priority information, surrounding AP information, and data amount information to the WS 101 before data transmission is started. These information items are included in the transmission notification. The communicator 601 receives first control information, second control information, connection instruction information, clock time information, and third control information from the WS 101. These information items are included in the instruction notification transmitted from the WS 101.

For example, the external terminal is a capsule endoscope (examination terminal). The external terminal has an image sensor, a control unit, and a communicator. The image sensor acquires examination data. The control unit controls the entire system of the external terminal. The communicator performs wireless communication with the STA. The communicator transmits the examination data acquired by the image sensor to the STA.

Figure 7:
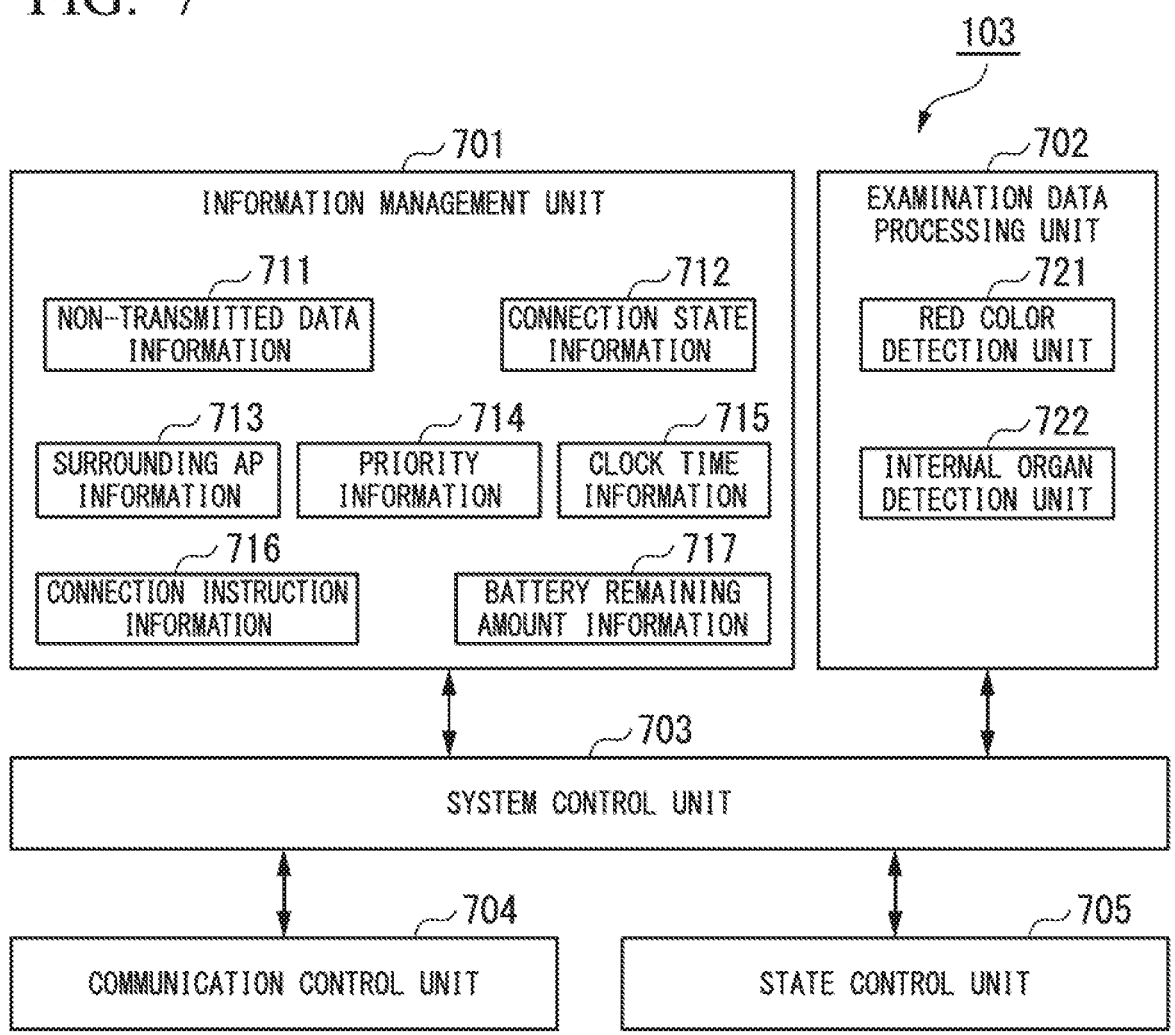
FIG. 7 is a block diagram showing a software configuration of the STA according to the embodiment of the present invention.

FIG. 7 shows a software configuration of an STA 103 (client) that is an examination-and-treatment device. Configurations of an STA 104, an STA 106, and an STA 107 are the same as the configuration of the STA 103. Therefore, only the configuration of the STA 103 will be described. Each component shown in FIG. 7 corresponds to a process generated by the CPU 603 executing a program. As shown in FIG. 7, the STA 103 has an information management unit 701, an examination data processing unit 702 (examination data processor), a system control unit 703 (data processor), a communication control unit 704 (communication controller), and a state control unit 705 (state controller).

The information management unit 701 manages non-transmitted data information 711, connection state information 712, surrounding AP information 713, priority information 714, clock time information 715, connection instruction information 716, and battery remaining amount information 717.

The non-transmitted data information 711 indicates the amount of data, which has not been completely transmitted to the WS 101, of the examination data received from the external terminal. The information management unit 701 acquires the non-transmitted data information 711 by subtracting the amount of the examination data transmitted to the WS 101 from the amount of the examination data received from the external terminal. The connection state information 712 indicates a connection state of the STA 103. The connection state information 712 includes information indicating whether or not the STA 103 is being connected to the network. In a case in which the STA 103 is being connected to the network, the connection state information 712 indicates an SSID, a BSSID (MAC address), and a channel of the access point to which the STA 103 is being connected. The surrounding AP information 713 indicates an SSID, a BSSID (MAC address), and a channel of an access point to which the STA 103 can be connected.

The priority information 714 indicates a priority of the STA 103. The priority information 714 is at least one of position information, abnormality information, and operation information. The clock time information 715 indicates a clock time when data transmission via an access point to which the STA is being connected may be started. That is, the clock time information 715 indicates a wake-up clock time of the STA 103 when the STA 103 is in the resting state. The clock time information 715 is included in an instruction notification received from the WS 101. The connection instruction information 716 indicates an instruction to connect to the access point indicated by the surrounding AP information. The connection instruction information 716 is included in the instruction notification received from the WS 101. The battery remaining amount information 717 indicates a remaining amount of the battery 606.

The examination data processing unit 702 generates position information and abnormality information on the basis of the examination data. The examination data processing unit 702 has a red color detection unit 721 and an internal organ detection unit 722. The red color detection unit 721 performs image processing on the examination data received from the external terminal and extracts features with a red color from color information of the examination data. In this manner, the red color detection unit 721 detects whether or not bleeding has occurred. In a case in which bleeding has been detected, the red color detection unit 721 generates abnormality information. The internal organ detection unit 722 performs image processing on the examination data received from the external terminal and extracts features of an internal organ from shape information of the examination data. In this manner, the internal organ detection unit 722 detects whether or not a target internal organ has been reached from the examination data. In a case in which it is detected that the target internal organ has been reached from the examination data, the internal organ detection unit 722 generates position information corresponding to the internal organ.

The system control unit 703 performs various kinds of processing. For example, the system control unit 703 requests data transmission to the WS 101 on the basis of information managed by the information management unit 701. The system control unit 703 provides an instruction to transmit a transmission notification or starting/ending data transmission to the communication control unit 704. The system control unit 703 provides notifications of the abnormality information and the position information generated by the examination data processing unit 702 as priority information to the WS 101. In a case in which a predetermined operation by the user via the input unit 602 has occurred, the system control unit 703 generates operation information. The predetermined operation is an instruction operation for performing data transmission with priority. The system control unit 703 provides a notification of the generated operation information as the priority information to the WS 101. The system control unit 703 reduces the amount of data when the remaining amount of the battery 606 becomes less than a predetermined amount. Alternatively, the system control unit 703 provides an instruction to stop communication to the communication control unit 704 when the remaining amount of the battery 606 becomes less than the predetermined amount. The system control unit 703 provides an instruction to control a state of the communicator 601 to the state control unit 705 in accordance with information included in the instruction notification received from the WS 101. The system control unit 703 provides an instruction to connect to the access point to the communication control unit 704. The system control unit 703 provides, to the communication control unit 704, an instruction to transmit a transmission request to the WS 101 every time non-transmitted data is generated.

The aforementioned predetermined amount means the amount of data which can be completely transmitted in a specific time with the data transmission ability (data transmission speed) of the STA 103. In a case in which the data transmission ability is 100 Mbps, for example, the amount of data which can be completely transmitted in five minutes is 3.7 GB according to Equation (1).

$$100 \text{ Mbps} \times 5 \text{ min} = 3.7 \text{ GB} \tag{1}$$

In a case in which 3 MB (100 KB×30 fps) of examination data is recorded in one second, the time required for the amount of data to reach 3.7 GB is about 20 minutes according to Equation (2).

$$3.7 \text{ GB}/3 \text{ MB} = \text{about } 20 \text{ minutes} \tag{2}$$

In the embodiment of the present invention, it is assumed as an example that the data transmission ability is 100 Mbps, that the target time is five minutes, and that the predetermined amount is 3.7 GB. The predetermined amount is the amount of data that is scheduled to be transmitted by the STA.

The communication control unit 704 transmits data or information to the WS 101 by using the communicator 601. Specifically the communication control unit 704 causes the communicator 601 to transmit the data or the information to the WS 101. In this manner, the communicator 601 transmits the data or the information to the WS 101. The communication control unit 704 receives the information from the WS 101 by using the communicator 601. Specifically, the communication control unit 704 causes the communicator 601 to receive the information transmitted from the WS 101. In this manner, the communicator 601 receives the information from the WS 101.

The communication control unit 704 generates a transmission notification including information that is managed by the information management unit 701 and information that is generated by the examination data processing unit 702. Specifically, the communication control unit 704 generates the transmission notification including connection AP information, priority information, surrounding AP information, and data amount information. The communication control unit 704 transmits the transmission notification to the WS 101 by using the communicator 601 before transmission of the examination data received from the external terminal is started. The communication control unit 704 transmits the examination data received from the external terminal to the WS 101 by using the communicator 605. The communication control unit 704 receives an instruction notification from the WS 101 by using the communicator 601. The communication control unit 704 extracts information from the instruction notification received from the WS 101. The information extracted from the instruction notification is output to the system control unit 703.

The communicator 601 receives the instruction notification including one of first control information, second control information, connection instruction information, and third control information. In a case in which the first control information or the third control information is received, the communication control unit 704 stops data transmission via an access point to which the STA 103 is being connected. In a case in which the second control information is received, the communication control unit 704 stands by for the data transmission via the access point to which the STA 103 is being connected. In a case in which the connection instruction information is received, the communication control unit 704 connects to the access point indicated by the surrounding AP information by using the communicator 601. The communication control unit 704 transmits data to the WS 101 by using the communicator 601 via the connected access point. The instruction notification including one of the first control information and the second control information includes clock time information. In a case in which one of the first control information and the second control information has been received and the clock time information has been received, the communication control unit 704 starts the data transmission via the access point to which the STA 103 is being connected at the clock time indicated by the clock time information.

The state control unit 705 controls a state of the communicator 601. In a case in which the data transmission is stopped on the basis of the first control information or in a case in which the data transmission is caused to be standing by on the basis of the second control information, the state control unit 705 brings the communicator 601 into the resting state. The power consumption of the communicator 601 in the resting state is smaller than the power consumption of the communicator 601 in the ordinary state. For example, the resting state is a state in which the communicator 601 is sleeping or has been turned off. The state control unit 705 wakes up the communicator 601 at the clock time (wake-up clock time) indicated by the clock time information.

The functions shown in FIG. 7 are realized by software by the CPU 603 reading and executing a program including commands defining these functions. The form in which this program is realized is similar to the form in which the program for realizing the functions of the WS 101 is realized.

The functions shown in FIG. 7 may be constituted as a processor. For example, the processor may be at least one of a CPU, a DSP, and a GPU. The processor may be at least one of an ASIC and an FPGA. The functions shown in FIG. 7 may include one or a plurality of processors.

(Communication Sequence)

Figure 8:
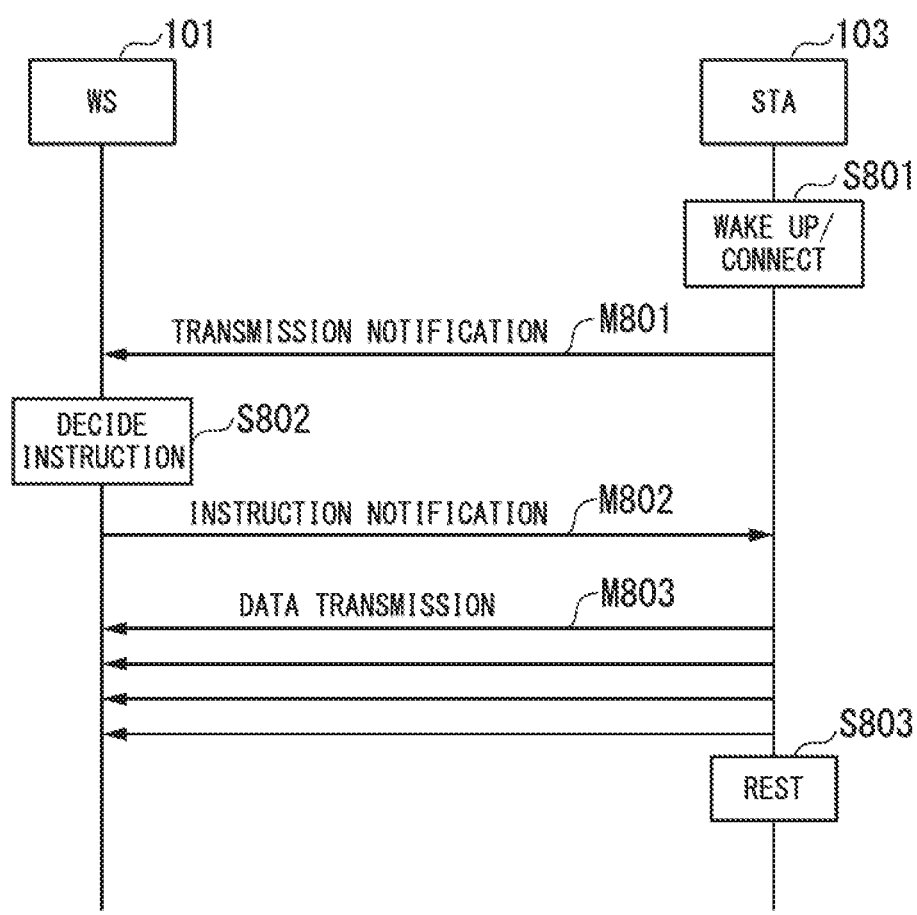
FIG. 8 is a sequence diagram showing a communication sequence between the WS and the STA according to the embodiment of the present invention.
Figure 9:
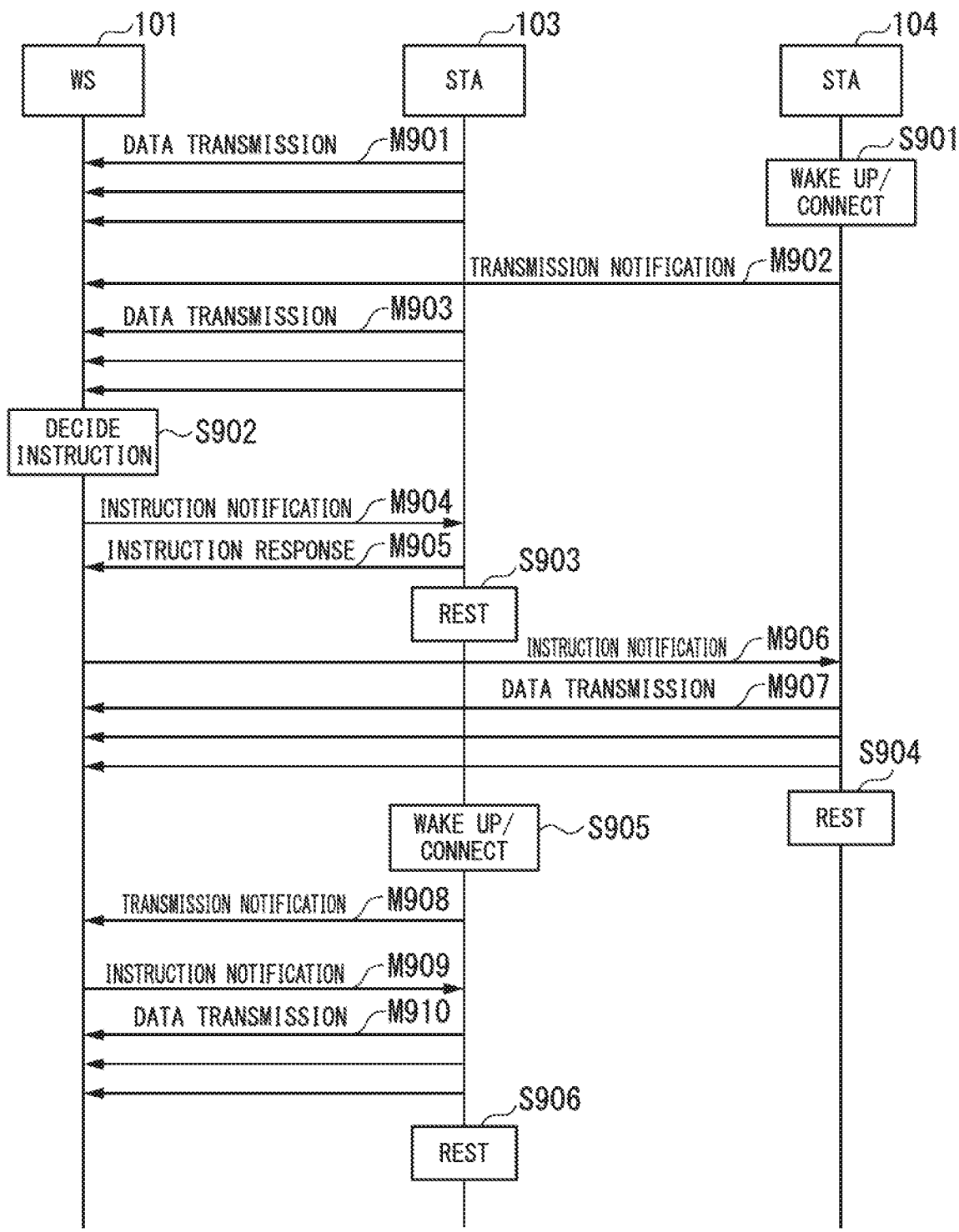
FIG. 9 is a sequence diagram showing the communication sequence between the WS and the STA according to the embodiment of the present invention.
Figure 10:
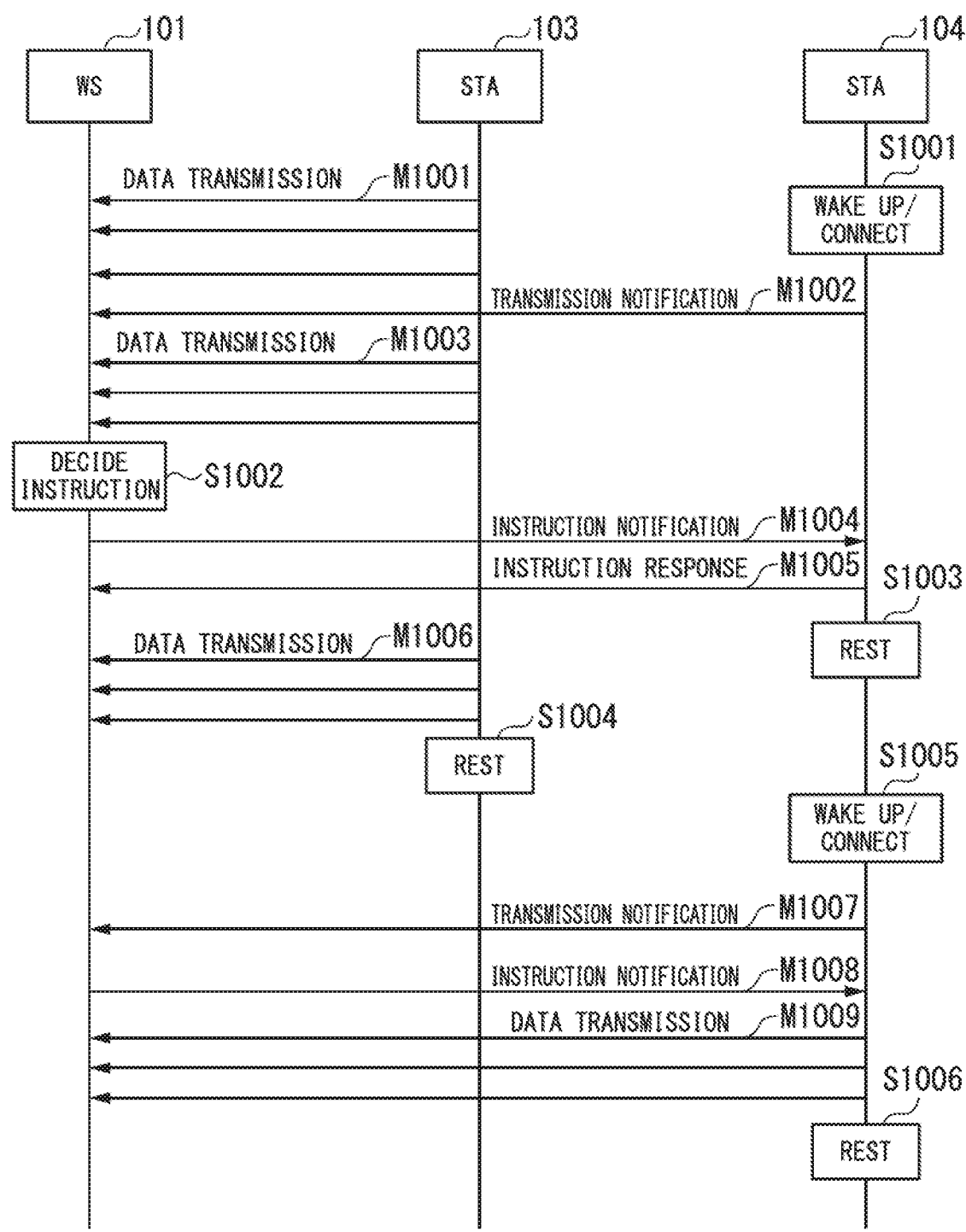
FIG. 10 is a sequence diagram showing the communication sequence between the WS and the STA according to the embodiment of the present invention.

FIGS. 8 to 10 show a communication sequence between the WS 101 and the STA 103 or the STA 104. A basic communication sequence between the WS 101 and the STA 103 will be described with reference to FIG. 8. It is assumed that the WS 101 and the STA 103 constitute a network that is connected via the AP 102 shown in FIG. 1.

The STA 103 wakes up the communicator 601 by using the state control unit 705. The STA 103 searches for an access point that is present in surroundings of the STA 103 by using the communicator 601. As a result of the searching, the STA 103 may recognize that the AP 102 is present in the surroundings of the STA 103. The STA 103 connects to the searched for AP 102 by using the communicator 601 (S801).

The STA 103 transmits a transmission notification (M801) to the WS 101 by using the communicator 601. The transmission notification includes connection AP information, priority information, surrounding AP information, data amount information, and an identification ID of the STA 103. The connection AP information includes information of the access point indicated by the connection state information 712. The priority information includes one of position information, abnormality information, and operation information. The surrounding AP information includes information of the access point indicated by the surrounding AP information 713. The data amount information includes information of the amount of data indicated by the non-transmitted data information 711. The transmission notification is transmitted to a broadcasting address. The WS 101 determines whether or not the STA which has requested to start the data transmission by the transmission notification is an STA that forms a pair with the WS 101 itself, on the basis of the identification ID included in the transmission notification. In this manner, the WS 101 can avoid communication with an incorrect counterpart even in a case in which there is another combination between a WS and an STA on the network.

The WS 101 decides an instruction for the STA 103 on the basis of the information included in the transmission notification and information of another STA that the WS 101 holds (S802). The WS 101 transmits an instruction notification (M802) to the STA 103 by using the communicator 405. The instruction notification may include permission information. The permission information indicates permission of data transmission. Alternatively, the instruction notification includes one of first control information and second control information. In a case in which the instruction notification includes the first control information or the second control information, the instruction notification includes an instruction to cause the communicator 601 to rest and clock time information. Alternatively, in a case in which the instruction notification includes the first control information or the second control information, the instruction notification includes connection instruction information. In the sequence shown in FIG. 8, the instruction notification (M802) includes permission information.

When the transmission notification (M801) is transmitted, the STA 103 cannot recognize the WS 101. Therefore, the transmission notification (M801) is transmitted to the broadcasting address. The STA 103 can recognize an address of the WS 101, which is a destination of the data, by receiving the instruction notification (M802) from the WS 101. The method of ascertaining the address of the counterpart of communication from a response to a message transmitted to the broadcasting address is a typical way. Therefore, detailed description thereof will be omitted. The STA 103, which has been permitted to perform data transmission by the instruction notification (M802), starts the data transmission (M803). After the data of the amount provided by the transmission notification (M801) is completely transmitted, the STA 103 causes the communicator 601 to rest by using the state control unit 705 (S803).

FIG. 9 shows a sequence in a case in which there is no room in a communication band of the communication path through which the STA 103 is transmitting data and the STA 104 requests to start data transmission with priority through the same communication path. The STA 103 is performing data transmission (M901) to the WS 101. The STA 104 wakes up the communicator 601 by the state control unit 705 and connects to the AP 102 by using the communicator 601

(S901). The STA 104 transmits a transmission notification (M902) to the WS 101 by using the communicator 601.

The STA 104 cannot ascertain that the STA 103 is transmitting data to the WS 101. Therefore, the STA 104 requests data transmission to the WS 101 at an arbitrary timing.

The WS 101 receives the data transmitted from the STA 103 by data transmission (M903) at a timing when the transmission notification (M902) is received from the STA 104. The WS 101 continues a current operation until the instruction is decided. The WS 101 decides an instruction for each STA (S902) after the transmission notification (M902) is received from the STA 104. The WS 101 has already recognized the STA 103 and the STA 104 at a timing when the decision processing is started on the basis of the transmission notification. The WS 101 determines a status of data transmission from each STA on the basis of data amount information received from each STA and the amount of data received from each STA. The STA 103 is the first client that has already started the data transmission to the WS 101. The STA 104 is the second client that is standing by for the data transmission to the WS 101.

In a case in which the priority information is included in the transmission notification (M902), the WS 101 transmits an instruction notification (M904) to the STA 103 by using the communicator 405 in order to receive data with priority from the STA 104. The instruction notification (M904) includes first control information, an instruction to cause the communicator 601 to rest, and clock time information. The instruction notification (M904) is for providing an instruction to stop the data transmission and causing the communicator 601 to rest to the STA 103. The STA 103 receives the instruction notification (M904) from the WS 101 by using the communicator 601 and transmits an instruction response (M905) to the WS 101 by using the communicator 601. The instruction response indicates that the STA 103 is aware of the instruction. After the instruction response (M905) is transmitted, the STA 103 causes the communicator 601 to rest by the state control unit 705 (S903).

The WS 101 recognizes that the data transmission by the STA 103 has been stopped by receiving the instruction response (M905). The WS 101 transmits an instruction notification (M906) including permission information to the STA 104 by using the communicator 405. The instruction notification (M906) is for providing an instruction for starting data transmission to the STA 104. The STA 104 starts data transmission (M907) on the basis of the instruction notification (M906) from the WS 101. After the data of the amount provided by the transmission notification (M902) is completely transmitted, the STA 104 causes the communicator 601 to rest by the state control unit 705 (S904).

The STA 103 wakes up the communicator 601 by the state control unit 705 at the clock time indicated by the clock time information included in the instruction notification (M904) and connects to the AP 102 by using the communicator 601 (S905). The STA 103 transmits a transmission notification (M908) to the WS 101 by using the communicator 601. The WS 101 recognizes completion of the data transmission by the STA 104 in response to the fact that the data of the amount indicated by the data amount information received from the STA 104 has been received from the STA 104. Therefore, the WS 101 permits data transmission by the STA 103 when the transmission notification (M908) is received.

The WS 101 transmits an instruction notification (M909) to the STA 103 by using the communicator 405. The instruction notification (M909) includes permission information. The STA 103 starts data transmission (M910) on the basis of the instruction notification (M909) from the WS 101. After the data of the amount provided by the transmission notification (M908) is completely transmitted, the STA 103 causes the communicator 601 to rest by the state control unit 705 (S906).

FIG. 10 shows a sequence in a case in which there is no room in a communication band of the communication path through which the STA 103 is transmitting data and the STA 104 requests to start data transmission with priority through the same communication path. The point that the priority information is not included in the transmission notification provided by the STA 104 to the WS 101 is a difference between FIGS. 9 and 10.

The STA 103 performs data transmission (M1001) to the WS 101. The STA 104 wakes up the communicator 601 by the state control unit 705 and connects to the AP 102 by using the communicator 601 (S1001). The STA 104 transmits a transmission notification (M1002) to the WS 101 by using the communicator 601.

The WS 101 receives data transmitted from the STA 103 by the data transmission (M1003) at a timing when the transmission notification (M1002) is received from the STA 104. The WS 101 continues a current operation until the instruction is decided. The WS 101 receives the transmission notification (M1002) from the STA 104 and then decides an instruction for each STA (S1002).

In a case in which the priority information is not included in the transmission notification (M1002), it is not necessary for the WS 101 to place priority on the data transmission by the STA 104 rather than the data transmission by the STA 103. The WS 101 transmits an instruction notification (M1004) to the STA 104 by using the communicator 405. The instruction notification (M1004) includes second control information, an instruction to cause the communicator 601 to rest, and clock time information. The instruction notification (M1004) is for providing an instruction to stand by for the data transmission and causing the communicator 601 to rest to the STA 104. The STA 104 receives the instruction notification (M1004) from the WS 101 by using the communicator 601 and transmits an instruction response (M1005) to the WS 101 by using the communicator 601. After the instruction response (M1005) is transmitted, the STA 104 causes the communicator 601 to rest by the state control unit 705 (S1003).

The STA 103 does not receive any instruction from the WS 101 while communication between the WS 101 and the STA 104 occurs. Therefore, the STA 103 continues data transmission (M1006). After the data transmission (M1006) of the amount of data provided by the transmission notification is completed, the STA 103 causes the communicator 601 to rest by the state control unit 705 (S1004).

The STA 104 wakes up the communicator 601 by the state control unit 705 at a clock time indicated by the clock time information included in the instruction notification (M1004) and connects to the AP 102 by using the communicator 601 (S1005). The STA 104 transmits a transmission notification (M1007) to the WS 101 by using the communicator 601. The WS 101 recognizes that the data transmission by the STA 103 has been completed in response to the fact that the data of the amount indicated by the data amount information received from the STA 103 has been received from the STA 103. Therefore, the WS 101 permits data transmission by the STA 104 when the transmission notification (M1007) is received.

The WS 101 transmits an instruction notification (M1008) to the STA 104 by using the communicator 405. The instruction notification (M1008) includes permission information. The STA 104 starts data transmission (M1009) on the basis of the instruction notification (M1008) from the WS 101. After the data of the amount provided by the transmission notification (M1007) is completely transmitted, the STA 104 causes the communicator 601 to rest by the state control unit 705 (S1006).

(Operations of WS 101)

Figure 11:
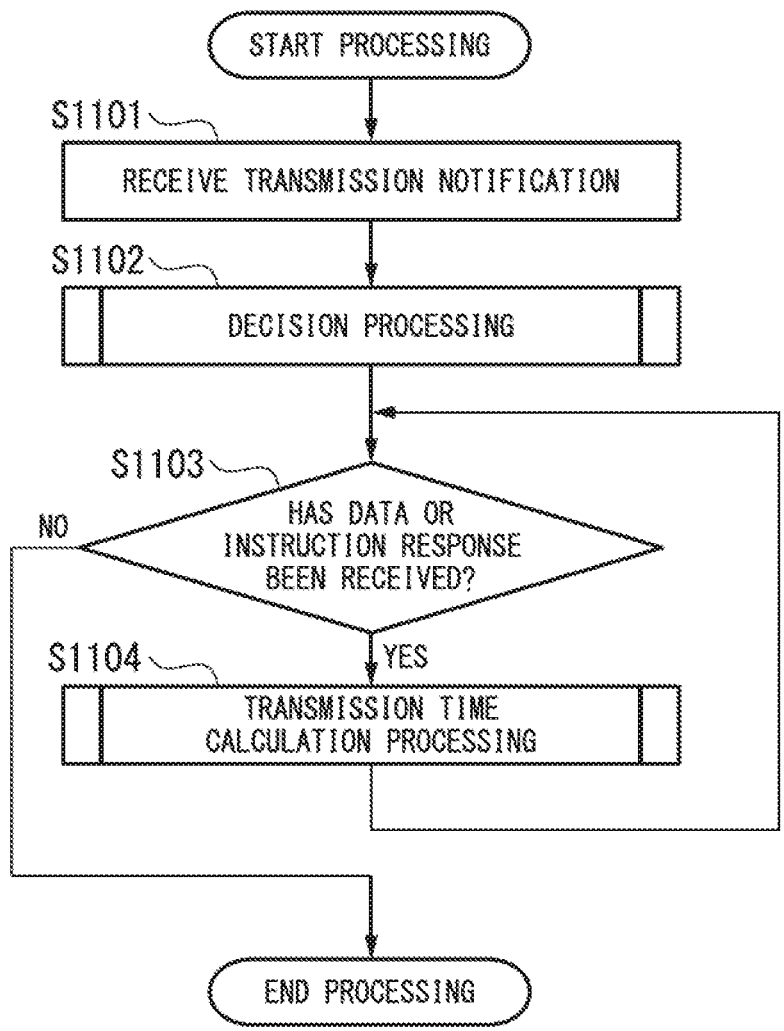
FIG. 11 is a flowchart showing an operation procedure of the WS according to the embodiment of the present invention.
Figure 12:
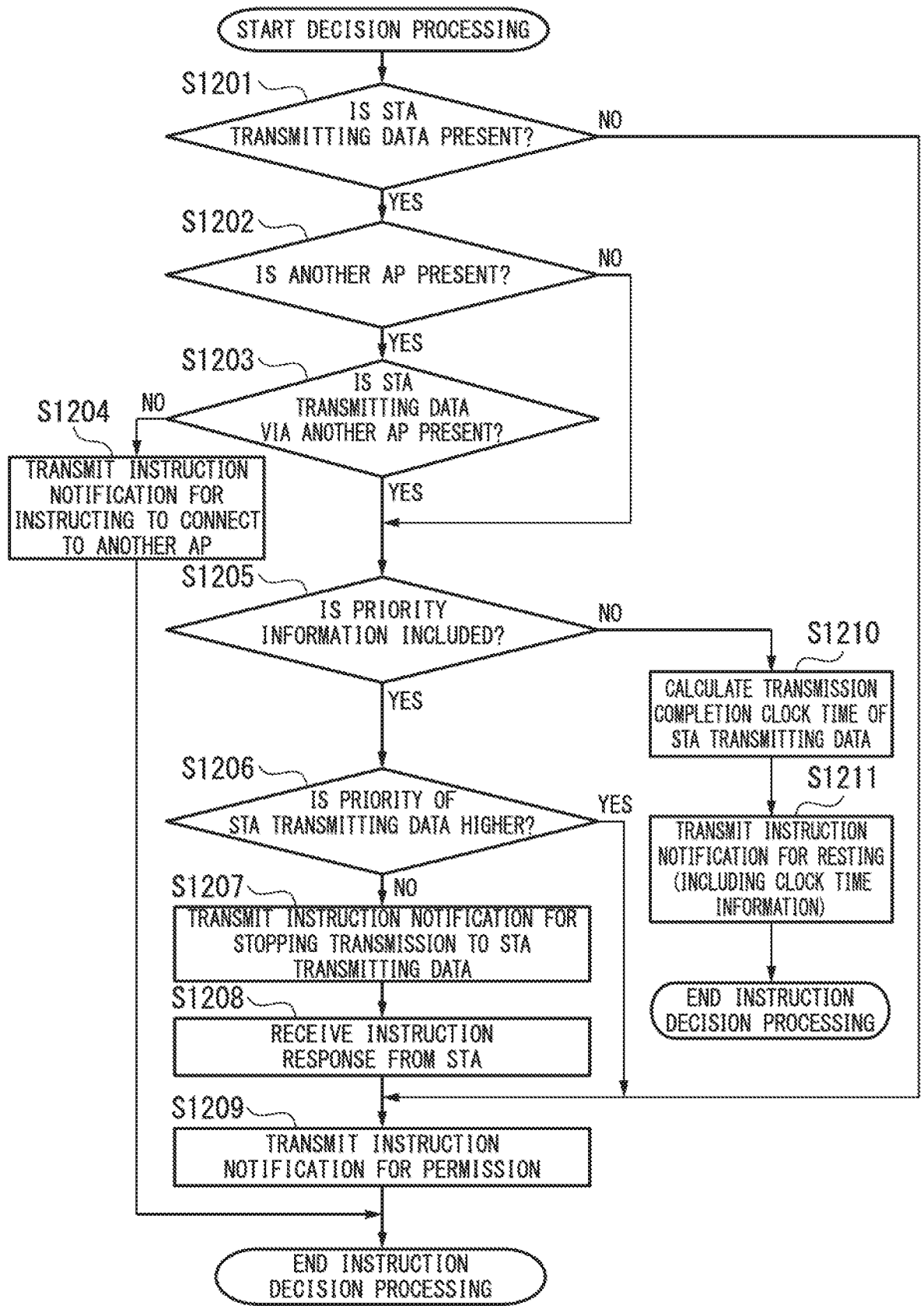
FIG. 12 is a flowchart showing an operation procedure of the WS according to the embodiment of the present invention.
Figure 13:
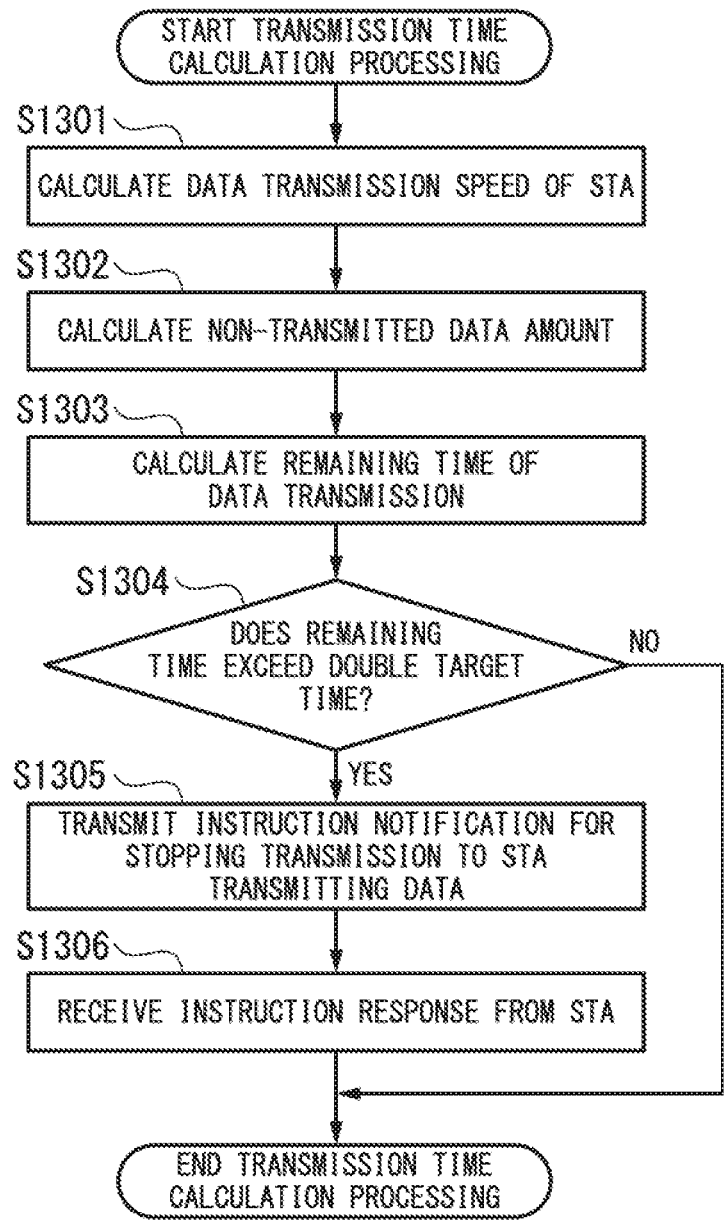
FIG. 13 is a flowchart showing an operation procedure of the WS according to the embodiment of the present invention.

FIGS. 11 to 13 show an operation procedure of the WS 101. As shown in FIGS. 1 to 3, the WS 101 is constantly connected to the network. The WS 101 can always receive notifications from each STA. The STA 103 is connected to the AP 102 and performs data transmission. Operations of the WS 101 in a case in which the STA 104 is connected to the AP 102 and transmits a transmission notification to the WS 101 will be described.

As shown in FIG. 11, the communication control unit 504 receives a transmission notification from the STA 104 by using the communicator 405 (S1101.) The decision unit 502 performs the decision processing on the basis of information included in the received transmission notification (S1102). The decision unit 502 decides an instruction for the STA 104 by the decision processing.

FIG. 12 shows an operation procedure of the WS 101 in the decision processing. Operations of the WS 101 in the decision processing will be described with reference to FIG. 12.

The decision processing unit 511 determines whether or not an STA that is transmitting data is present on the basis of connection AP information included in the transmission notification and STA information managed by the STA information management unit 501. That is, the decision processing unit 511 determines whether or not a first condition is satisfied (S1201). The first condition indicates that an access point indicated by the connection AP information received from the first client (STA 103) is the same as an access point indicated by the connection AP information received from the second client (STA 104). In this manner, the decision processing unit 511 determines whether or not there is an STA that is transmitting data by using the same communication path as the communication path that is being used by the STA 104 which has requested to start the data transmission by the transmission notification.

In a case in which the access points indicated by the respective connection AP information items received from different STAs are different from each other in S1201, the decision processing unit 511 decides to permit data transmission. Alternatively, in a case in which no connection AP information has been received from STAs other than the STA 104, the decision processing unit 511 decides to permit data transmission. In a case in which the decision processing, unit 511 decides to permit data transmission, the communication control unit 504 generates an instruction notification including permission information. The communication control unit 504 transmits an instruction notification to the STA 104 by using the communicator 405 (S1209). The decision processing ends by the processing in S1209 being performed.

In a case in which the access points indicated by the connection AP information items received from the different STAs are the same in S1201, the decision processing unit 511 decides to refuse data transmission. In a case in which the decision processing unit 511 decides to refuse data transmission, the decision processing unit 511 determines whether or not access points other than the AP 102, to which the STA 104 is being connected, are present on the basis of the surrounding AP information included in the transmission notification from the STA 104 (S1202). In a case in which surrounding AP information is included in the transmission notification in S1202, that is, in a case in which the surrounding AP information has been received, the decision processing unit 511 determines that access points other than the AP 102, to which the STA 104 is being connected, are present. In a case in which the surrounding AP information is not included in the transmission notification in S1202, that is, in a case in which the surrounding AP information has not been received, the decision processing unit 511 determines that no access points other than the AP 102, to which the STA 104 is being connected, are present. In a case in which no access points other than the AP 102, to which the STA 104 is being connected, are present in S1202, processing in S1205 is performed. The processing in S1205 will be described later.

In a case in which an access point (AP 105) other than the AP 102, to which the STA 104 is being connected, is present in S1202, the decision processing unit 511 determines whether or not other STAs that are transmitting data are present in a transmission path via the access point (AP 105) detected in S1202 on the basis of the STA information managed by the STA information management unit 501 (S1203). In a case in which no other STAs are present in S1203, the communication control unit 504 generates an instruction notification including connection instruction information. The connection instruction information indicates an instruction to connect to the access point detected in S1202, that is, the access point indicated by the surrounding AP information. The connection instruction information may include information of the access point indicated by the surrounding AP information. The communication control unit 504 transmits an instruction notification to the second client (STA 104) via the communicator 405 (S1204). The decision processing ends by the processing in S1204 being performed.

In a case in which other STAs are present in S1203, the decision processing unit 511 determines whether or not priority information is included in the transmission notification from the STA 104. That is, the decision processing unit 511 determines whether or not a third condition is satisfied (S1205). The third condition indicates that priority information has not been received from the second client (STA 104). In a case in which the priority information is included in the transmission notification in S1205, the decision processing unit 511 determines that the priority information has been received. In a case in which the priority information is not included in the transmission notification in S1205, the decision processing unit 511 determines that the priority information has not been received.

In a case in which the priority information has not been received, the decision unit 502 decides to cause the STA 104, which has requested to start data transmission by the transmission notification, to stand by for data transmission. The clock time calculation unit 512 calculates a clock time when the data transmission by the STA 103 that is transmitting the data is to be completed (S1210). The clock time calculation unit 512 measures a data transmission ability (data transmission speed) of the STA 103 in S1210. The clock time calculation unit 512 calculates a length of time necessary for transmitting data that has not yet been transmitted on the basis of the measurement value of the data transmission ability, the amount of data indicated by the data amount information received from the STA 103, and the amount of the data that has already been received from the STA 103. The clock time calculation unit 512 calculates a clock time when the data transmission by the STA 103 is to be completed by adding the calculated time to a current clock time.

After the clock time when the data transmission is to be completed is calculated, the communication control unit 504 generates an instruction notification to the STA 104. The instruction notification includes second control information indicating an instruction to stand by for data transmission, an instruction to cause the communicator 601 to rest, and clock time information indicating a wake-up clock time. The clock time calculated in S1210 is the wake-up clock time. The communication control unit 504 transmits an instruction notification to the STA 104 by using the communicator 405 (S1211). The decision processing ends by the processing in S1211 being performed.

In a case in which the priority information is included in the transmission notification in S1205, the decision processing unit 511 determines whether or not a priority of the STA 103 that is transmitting data is higher than a priority of the STA 104 that has requested to start data transmission by the transmission notification. That is, the decision processing unit 511 determines whether or not a second condition is satisfied (S1206). The second condition indicates that a priority indicated by the priority information received from the first client (STA 103) is lower than a priority indicated by the priority information received from the second client (STA 104).

In a case in which the priority of the STA 103 that is transmitting data is higher than the priority of the STA 104 that has requested to start data transmission by the transmission notification in S1206, the decision processing unit 511 decides not to cause the STA 103 to stop the data transmission and to permit data transmission by the STA 104. The communication control unit 504 generates an instruction notification including permission information. The communication control unit 504 transmits the instruction notification to the STA 104 by using the communicator 405 (S1209). The decision processing ends by the processing in S1209 being performed.

In a case in which the priority of the STA 103 that is transmitting data is lower than the priority of the STA 104 that has requested to start data transmission by the transmission notification in S1206, the decision processing unit 511 decides to cause the STA 103 to stop the data transmission. Alternatively, in a case in which the priority information is not included in the transmission notification from the STA 103 that is transmitting data, that is, in a case in which the priority information has not been received from the STA 103, the decision processing unit 511 decides to cause the STA 103 to stop the data transmission. The communication control unit 504 generates an instruction notification including first control information indicating an instruction to stop the data transmission, an instruction to cause the communicator 601 to rest, and clock time information indicating a wake-up clock time. The wake-up clock time is calculated as follows. The clock time calculation unit 512 measures a data transmission ability (data transmission speed) of the STA 103. The clock time calculation unit 512 calculates a length of time necessary for transmitting data, which has not yet been transmitted, on the basis of the measurement amount of the data transmission ability and the amount of data indicated by the data amount information received from the STA 103. The clock time calculation unit 512 calculates a clock time when the data transmission by the STA 103 is to be completed by adding the calculated time to a current clock time. The calculated clock time when the data transmission is to be completed is the wake-up clock time. The communication control unit 504 transmits an instruction notification to the STA 103 by using the communicator 405 (S1207).

After the instruction notification is transmitted in S1207, the communication control unit 504 receives an instruction response to the instruction notification from the STA 103 by using the communicator 405 (S1208). After the instruction response is received, the decision processing unit 511 permits data transmission by the STA 104. The communication control unit 504 generates an instruction notification including permission information. The communication control unit 504 transmits the instruction notification to the STA 104 by using the communicator 405 (S1209). The decision processing ends by the processing in S1209 being performed.

As described above, the decision processing unit 511 determines whether or not the first condition is satisfied (S1201). Further, the decision processing unit 511 determines whether or not any one of the second condition and the third condition satisfied (S1206, S1205). In a case in which the first condition and the second condition are satisfied, the decision processing unit 511 decides to cause the STA 103 that is transmitting data to stop the data transmission (S1207). The communication control unit 504 transmits first control information indicating an instruction to stop the data transmission to the STA 103 by using the communicator 405 (S1207). In a case in which the first condition and the third condition are satisfied, the decision processing unit 511 decides to cause the STA 104, which has requested to start data transmission by the transmission notification, to stand by for data transmission (S1210). The communication control unit 504 transmits second control information indicating an instruction to stand by for data transmission to the STA 104 by using the communicator 405 (S1211).

In a case in which the first condition is satisfied and the surrounding AP information has been received, the communication control unit 504 transmits connection instruction information to the STA 104 by using the communicator 405 (S1204). Specifically, in a case in which the first condition is satisfied and no STA that is being connected to the access point indicated by the surrounding AP information is present, the communication control unit 504 transmits the connection instruction information to the STA 104 by using the communicator 405 (S1204). The connection instruction information indicates an instruction to connect to the access point indicated by the surrounding AP information.

In a case in which the first condition is satisfied and the surrounding AP information has not been received, the decision processing unit 511 determines whether or not any one of the second condition and the third condition is satisfied (S1206, S1205). Alternatively, in a case in which the first condition is satisfied, the surrounding AP information has been received, and an STA that is being connected to the access point indicated by the surrounding AP information is present, the decision processing unit 511 determines whether or not any one of the second condition and the third condition is satisfied (S1206, S1205). A method of determining a state in accordance with the second condition and the third condition is as described above.

In a case in which the first condition is satisfied and a priority indicated by the priority information received from the STA 103 is higher than a priority indicated by the priority information received from the STA 104, the decision processing unit 511 decides to permit data transmission by the STA 104 that has requested to start data transmission by the transmission notification (S1209). In this case, the STA 103 that is transmitting data continues the data transmission.

An instruction for each STA is decided, and a notification of the details of the instruction is provided to each STA by the aforementioned decision processing.

The operations shown in FIG. 11 will be described again. After the decision processing (S1102) is performed, the communication control unit 504 receives data or an instruction response from the STA (the STA 103 or the STA 104) by using the communicator 405. The decision processing unit 511 determines whether or not the data or the instruction response has been received from the STA (S1103). In a case in which the data or the instruction response has not been received in S1103, the processing ends. In a case in which the data or the instruction response has been received in S1103, the transmission time calculation unit 513 performs transmission time calculation processing for calculating a remaining time of the data transmission by the STA that is transmitting data (S1104). The determination in S1103 is performed after the transmission time calculation processing is performed.

FIG. 13 shows an operation procedure of the WS 101 in the transmission time calculation processing. Operations of the WS 101 in the transmission time calculation processing will be described with reference to FIG. 13.

In the transmission time calculation processing, the transmission time calculation unit 513 calculates a remaining time until receiving data of the amount indicated by the data amount information included in the transmission notification is to be completed. The transmission time calculation unit 513 calculates this remaining time every time data is received from the STA. Hereinafter, a calculation method will be described.

The transmission time calculation unit 513 calculates a data transmission speed of the STA (S1301). An actual data transmission speed varies in accordance with a communication state in the network even in a case in which the data transmission ability is 100 Mbps. Therefore, the transmission time calculation unit 513 measures the data transmission speed when data transmission is actually performed. The transmission time calculation unit 513 calculates the data transmission speed on the basis of the amount of data received per unit time.

After the data transmission speed is calculated, the transmission time calculation unit 513 calculates the amount of data that has not yet been transmitted (S1302). The transmission time calculation unit 513 calculates the amount of data that has not yet been transmitted by subtracting a second data amount from a first data amount in S1302. The first data amount is the amount of data indicated by the data amount information received from the STA. The second data amount is the amount of data that has already been received from the STA.

After the amount of data that has not yet been transmitted is calculated, the transmission time calculation unit 513 calculates a remaining time of the data transmission by using Equation (3) on the basis of the data transmission speed and the amount of data that has not yet been transmitted (S1303).

$$\text{Remaining time} = \text{amount of data that has not yet been transmitted}/\text{data transmission speed} \quad (3)$$

The decision processing unit 511 determines whether or not the remaining time exceeds double a target time (S1304). In a case in which the target time is five minutes, for example, the transmission time calculation unit 513 determines whether or not the remaining time exceeds ten minutes in S1304. The determination in S1304 is not limited to the aforementioned example. In a case in which the remaining time does not exceed double the target time in S1304, the transmission time calculation processing ends. In a case in which the remaining time exceeds double the target time in S1304, transmission efficiency is poor. Therefore, the decision processing unit 511 decides to cause the STA that is transmitting data to stop the data transmission. The communication control unit 504 generates an instruction notification including third control information indicating an instruction to stop the data transmission and an instruction to cause the communicator 601 to rest. The communication control unit 504 transmits the instruction notification to the STA by using the communicator 405 (S1305).

After the instruction notification is transmitted in S1305 the communication control unit 504 receives an instruction response to the instruction notification from the STA by using the communicator 405 (S1306). The transmission time calculation processing ends by the processing in S1306 being performed.

The operations shown in FIG. 11 will be described again. In a case in which the remaining time exceeds double the target time in the transmission time calculation processing (S1104), an instruction to stop the data transmission is provided to the STA that is transmitting data. In this manner, no data is received from the STA (S1103). Therefore, the processing ends. In a case in which the remaining time is within double the target time, the data reception and the transmission time calculation processing are repeated until receiving data is completed.

(Operations of STA)

FIGS. 14 to 17 illustrate an operation procedure of the STA. Operations of the STA will be described. After power supply to the STA is activated, the STA can always communicate with an external terminal via the communicator 605.

Figure 14:
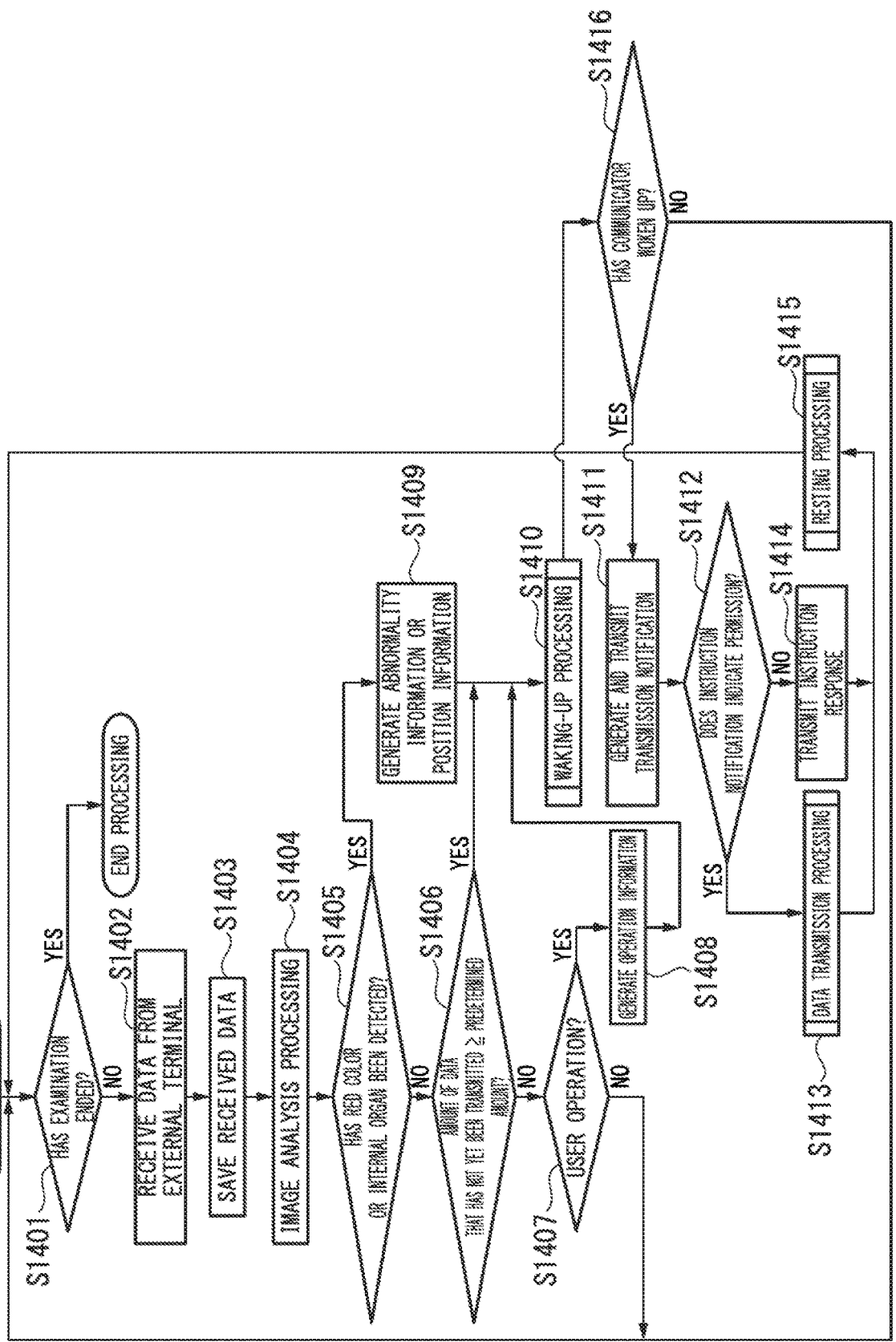
FIG. 14 is a flowchart showing an operation procedure of the STA according to the embodiment of the present invention.

As shown in FIG. 14, the system control unit 703 checks whether or not the examination has ended (S1401). For example, a cause of the end of the examination is a decrease in a battery remaining amount and interruption of data reception from the external terminal. When these states occur, the STA ends the processing.

In a case in which the aforementioned factors have not been detected, the communication control unit 704 receives examination data from the external terminal by using the communicator 605 (S1402). The system control unit 703 saves the received examination data in the recording unit 604 (S1403). The examination data processing unit 702 performs image analysis processing on the received examination data (S1404). In the image analysis processing, a typically known method is used. The examination data processing unit 702 performs shape feature extraction and color information extraction by performing extraction of feature points or the like in S1404.

After the image analysis processing is performed, the examination data processing unit 702 checks whether or not a red color or a specific internal organ has been detected by the image analysis processing (S1405). In a case in which the red color or the specific internal organ has been detected in S1405, the examination data processing unit 702 generates abnormality information or position information (S1409). The generated abnormality information or the position information is managed as priority information 714 by the information management unit 701. After the abnormality information or the position information is generated, processing in S1410 is performed. The processing in S1410 will be described later.

In a case in which the red color and the specific internal organ have not been detected in S1405, the system control unit 703 determines whether or not the amount of data that has not yet, been transmitted indicated by the non-transmitted data information 711 managed by the information management unit 701 is equal to or greater than a predetermined amount (S1406). The predetermined amount means the amount of data that is completely transmitted in a specific time by the data transmission ability of the STA. For example, the predetermined amount is represented by the aforementioned Equation (1). In a case in which the amount of data that has not yet been transmitted is equal to or greater than the predetermined amount in S1406, processing in S1410 is performed. The processing in S1410 will be described later.

In a case in which the amount of data that has not yet been transmitted is less than the predetermined amount in S1406, the system control unit 703 determines whether or not a predetermined operation by the user has occurred via the input unit 602 (S1407). In a case in which the user who is being examined voluntarily requires immediate transmission of current examination data to the WS 101 and analysis thereof, for example, the user can start the data transmission by operating the input unit 602. In a case in which the predetermined operation has not occurred in S1407, the determination in S1401 is performed. In a case in which the predetermined operation has occurred in S1407, the system control unit 703 generates operation information (S1408). The generated operation information is managed as priority information 714 by the information management unit 701.

After the operation information is generated, the system control unit 703 performs waking-up processing (S1410). In the waking-up processing, the system control unit 703 performs processing for waking up the communicator 601 in the resting state. The communicator 601, which has woken up, is brought into the ordinary state.

Figure 15:
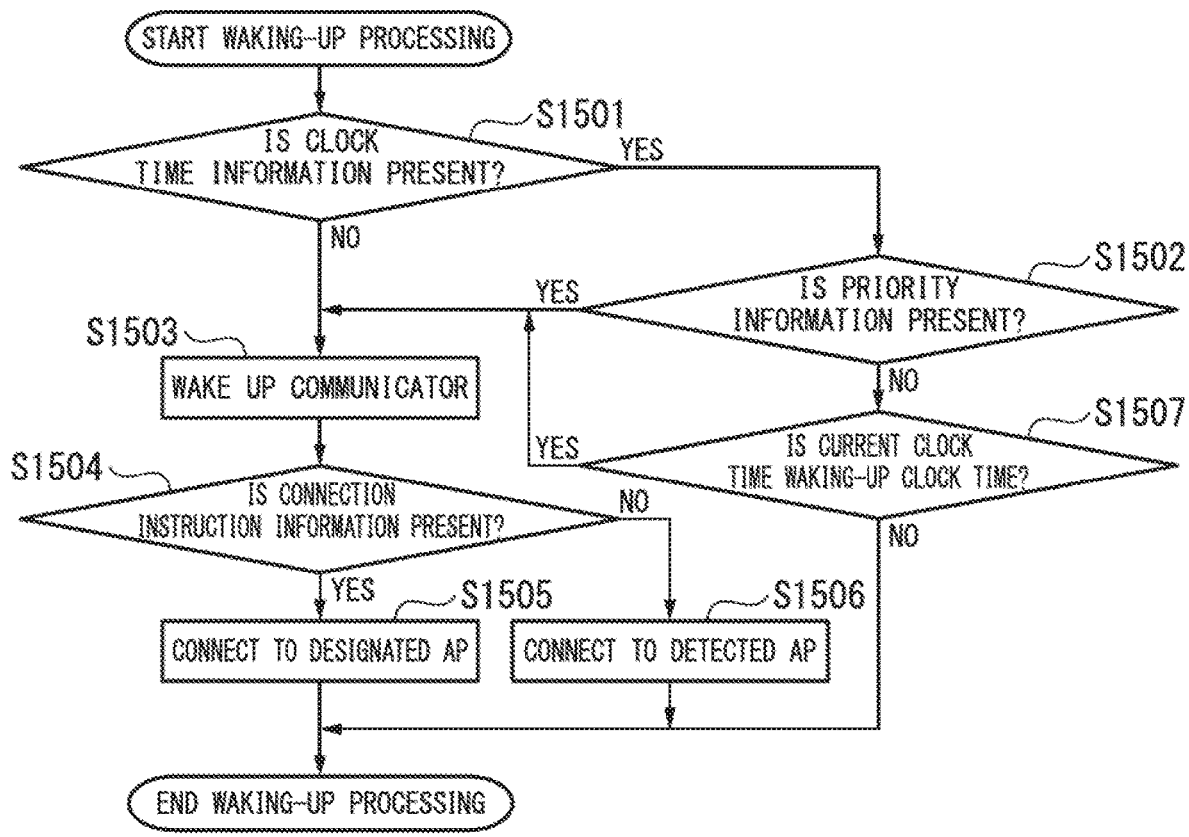
FIG. 15 is a flowchart showing an operation procedure of the STA according to the embodiment of the present invention.

FIG. 15 shows an operation procedure of the STA in the waking-up processing. Operations of the STA in the waking-up processing will be described with reference to FIG. 15. When the STA is not communicating with the WS 101, the communicator 601 is in the resting state. The system control unit 703 determines whether or not clock time information received from the WS 101 is present (S1501). In a case in which the clock time information has been received from the WS 101, the received clock time information is managed as clock time information 715 by the information management unit 701. In a case in which the clock time information is not present in S1501, processing in S1503 is performed. The processing in S1503 will be described later.

In a case in which the clock time information is present in S1501, the system control unit 703 determines whether or not priority information is present (S1502). In a case in which the priority information has been generated, the generated priority information is managed as the priority information 714 by the information management unit 701. In a case in which the priority information is present in S1502, processing in S1503 is performed. The processing in S1503 will be described later.

In a case in which the priority information is not present in S1502, the system control unit 703 determines whether or not the clock time indicated by the clock time information is the same as a current clock time. That is, the system control unit 703 determines whether or not the current clock time is the wake-up clock time (S1507). In a case in which the current clock time is not the wake-up clock time in S1507, the waking-up processing ends. In a case in which the current clock time is the wake-up clock time in S1507, the state control unit 705 wakes up the communicator 601 (S1503). In a case in which the communicator 601 has already woken up in S1503, the processing in S1503 is omitted.

After the communicator 601 wakes up, the system control unit 703 determines whether or not connection instruction information is present (S1504). In a case in which the connection instruction information has been received from the WS 101, the received connection instruction information is managed as connection instruction information 716 by the information management unit 701. In a case in which the connection instruction information is present in S1504, the communication control unit 704 causes the communicator 601 to connect to the access point indicated by the surrounding AP information 713 managed by the information management unit 701 (S1505). In a case in which the connection instruction information received from the WS 101 includes information of the access point, the communication control unit 704 may cause the communicator 601 to connect to the access point indicated by the connection instruction information. In a case in which the connection instruction information is not present in S1504, the communication control unit 704 detects an access point in surroundings of the STA by using the communicator 601. The communication control unit 704 causes the communicator 601 to connect to the detected access point (S1506). After connecting to the access point, the STA is brought into a state in which the STA can communicate with the WS 101. The waking-up processing ends by the processing in S1505 or S1506 being performed.

The operations shown in FIG. 14 will be described again. After the waking-up processing (S1410) is performed, the system control unit 703 determines whether or not the communicator 601 has woken up (S1416). The system control unit 703 determines whether or not the processing in S1503 has been performed in S1416. In a case in which the processing in S1503 has not been performed, the system control unit 703 determines that the communicator 601 has not woken up. In a case in which the processing in S1503 has been performed, the system control unit 703 determines that the communicator 601 has woken up.

In a case in which the communicator 601 has not woken up in S1416, the determination in 1401 is performed, in a case in which the communicator 601 has woken up in S1416, the communication control unit 704 generates a transmission notification and transmits the transmission notification to the WS 101 by using the communicator 601 (S1411). In a case in which the priority information is present, a transmission notification including the priority information is generated. In a case in which the priority information is not present, a transmission notification that includes no priority information is generated. In a case in which access points that are different from the access point to which the STA is being connected are present in the surroundings of the STA, a transmission notification including the surrounding AP information is generated. In a case in which no access points that are different from the access point to which the STA is being connected are present in the surroundings of the STA, a transmission notification that includes no surrounding AP information is generated. After the transmission notification is transmitted, the communication control unit 704 receives an instruction notification from the WS 101 by using the communicator 601. The system control unit 703 determines whether or not the instruction notification includes permission information. That is, the system control unit 703 determines whether or not the instruction notification indicates permission of data transmission (S1412).

In a case in which the instruction notification does not include permission information in S1412, that is, in a case in which the instruction notification includes one of the second control information and the connection instruction information, the communication control unit 704 transmits an instruction response to the WS 101 by using the communicator 601 (S1414). In this case, the communication control unit 704 stands by for data transmission via the access point to which the STA is being connected. In a case in which the instruction notification includes permission information in S1412, the system control unit 703 performs data transmission processing (S1413).

Figure 17:
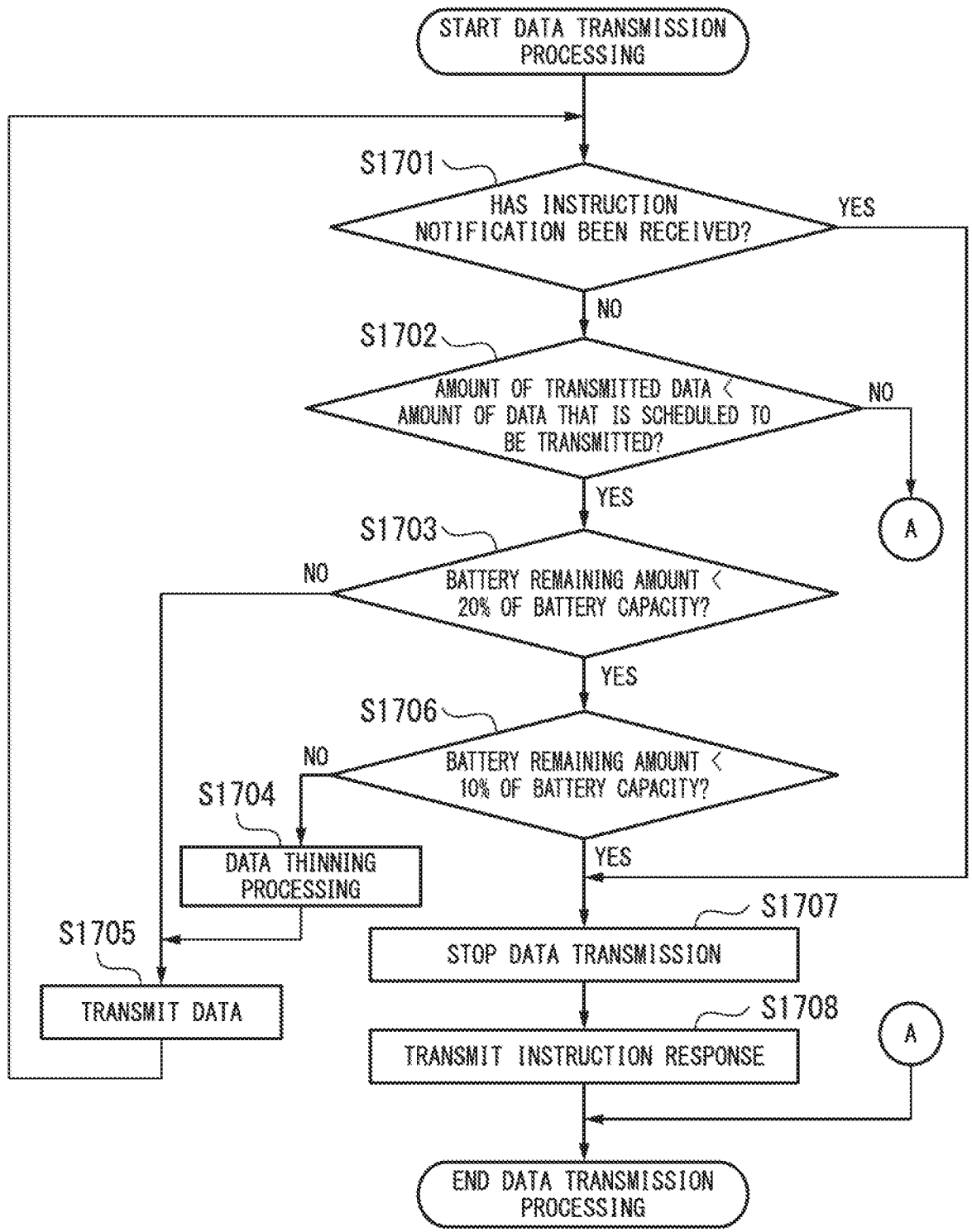
FIG. 17 is a flowchart showing an operation procedure of the STA according to the embodiment of the present invention.

FIG. 17 shows an operation procedure of the STA in the data transmission processing. Operations of the STA in the data transmission processing will be described with reference to FIG. 17. The system control unit 703 monitors a reception state such that an instruction notification can be received from the WS 101 while transmitting data. In a case in which the instruction notification is transmitted from the WS 101, the communication control unit 704 receives the instruction notification from the WS 101 by using the communicator 601. The system control unit 703 determines whether or not the instruction notification has been received while the data is being transmitted (S1701). In a case in which the instruction notification is transmitted from the WS 101 to the STA while the data transmission processing is being performed, the instruction notification includes one of the first control information and the third control information, which indicates an instruction to stop the data transmission. In a case in which the instruction notification has been received in S1701, the communication control unit 704 causes the communicator 601 to stop the data transmission. In this manner, the communicator 601 stops the data transmission (S1707). After the data transmission stops, the communication control unit 704 transmits an instruction response to the WS 101 by using the communicator 601 (S1708). The data transmission processing ends by the processing in S1708 being performed.

In a case in which the instruction notification has not been received in S1701, the system control unit 703 compares a first data amount with a second data amount. The first data amount is the amount of data indicated by the data amount information transmitted to the WS 101. That is, the first data amount is the amount of data that is scheduled to be transmitted. The second data amount is the amount of data that has already been transmitted. The system control unit 703 determines whether or not the second data amount is less than the first data amount (S1702).

In a case in which the second data amount is equal to or greater than the first data amount in S1702, the data transmission processing ends. In a case in which the second data amount is less than the first data amount in S1702, the system control unit 703 checks the battery remaining amount on the basis of the battery remaining amount information 717. The system control unit 703 determines whether or not the battery remaining amount is less than 20% of the battery capacity (S1703).

In a case in which the battery remaining amount is equal to or greater than 20% of the battery capacity in S1703, the communication control unit 704 transmits data (examination data) to the WS 101 by using the communicator 601 (S1705). Data of a transmission buffer size defined by a communication protocol is transmitted through data transmission at one time. In a case in which data transmission by TCP/IP is performed, for example, data of 1460 bytes is transmitted. Alternatively, image data corresponding to one frame that constructs a moving image may be transmitted through data transmission at one time. After the data is transmitted, the determination in S1701 is performed.

In a case in which the battery remaining amount is less than 20% of the battery capacity in S1703, the system control unit 703 determines whether or not the battery remaining amount is less than 10% of the battery capacity (S1706). In a case in which the battery remaining amount is less than 10% of the battery capacity in S1706, the communication control unit 704 causes the communicator 601 to stop the data transmission. In this manner, the communicator 601 stops the data transmission (S1707).

In a case in which the battery remaining amount is equal to or greater than 10% of the battery capacity in S1706, that is, in a case in which the battery remaining amount is equal to or greater than 10% and less than 20% of the battery capacity, the system control unit 703 performs data thinning processing (S1704). For example, the system control unit 703 performs control such that image data of only even numbered frames or odd numbered frames is transmitted in S1704. That is, frame thinning is performed. In this manner, the system control unit 703 reduces the amount of the data to be transmitted to the WS 101. After the data thinning processing is performed, the communication control unit 704 transmits thinned data to the WS 101 by using the communicator 601 (S1705).

Different processing is performed in accordance with the battery remaining amount as described above. Although the two threshold values are used for the battery remaining amount in the aforementioned example, the number of threshold values for the battery remaining amount may be three or more. The data thinning processing may be processing other than file thinning. For example, the system control unit 703 may reduce the amount of data by reducing specific information (brightness or saturation, for example) by image processing. Alternatively, the system control unit 703 may reduce the amount of data by using an image compression technology.

The operations shown in FIG. 14 will be described again. After the data transmission processing (S1413) or the transmission of the instruction response (S1414) is performed, resting processing is performed (S1415). After the resting processing is performed, the determination in S1401 is performed.

Figure 16:
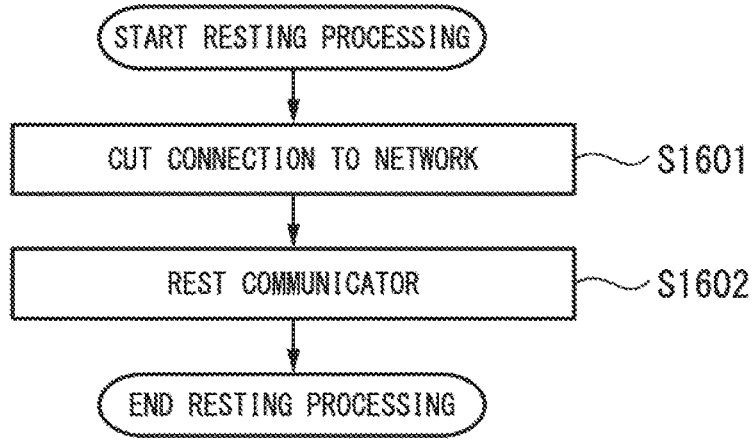
FIG. 16 is a flowchart showing an operation procedure of the STA according to the embodiment of the present invention.

FIG. 16 shows an operation procedure of the STA in the resting processing. Operations of the STA in the resting processing will be described with reference to FIG. 16. The communication control unit 704 stops connection to the access point to which the communicator 601 is being connected. In this manner the connection to the network is cut (S1601). After the connection to the network is cut, the state control unit 705 brings the communicator 601 into the resting state (S1602). The resting processing ends by the processing in S1602 being performed.

(Configurations and Effects)

As described above, the WS 101 (server) has the communicator 405, the decision unit 502, and the communication control unit 504. The communicator 405 receives data at an application level from the STA (client) (S1103) and receives connection AP information and priority information from the client before reception of the data is started (S1101). The STA is one of the first client and the second client. The first client is a terminal that has already started data transmission to the WS 101 at a timing when the decision processing (S1102) is started. The second client is a terminal that is standing by for the data transmission to the WS 101 at the timing when the decision processing is started. The connection AP information indicates an access point to which the client is being connected. The priority information indicates a priority of the client.

In the decision processing, the decision unit 502 determines whether or not the first condition is satisfied (S1201) and determines whether or not any one of the second condition and the third condition is satisfied (S1206, S1205). In a case in which the first condition and the second condition are satisfied, the decision unit 502 decides to cause the first client to stop the data transmission in the decision processing (S1207). In a case in which the first condition and the third condition are satisfied, the decision unit 502 decides to cause the second client to stand by for the data transmission in the decision processing (S1210). The first condition indicates that an access point indicated by the connection AP information received from the first client is the same as an access point indicated by the connection AP information received from the second client. The second condition indicates that a priority indicated by the priority information received from the first client is lower than a priority indicated by the priority information received from the second client. The third condition indicates that priority information has not been received from the second client.

In a case in which the decision unit 502 decides to cause the first client to stop the data transmission, the communication control unit 504 transmits the first control information to the first client by using the communicator 405 (S1207). In a case in which the decision unit 502 decides to cause the second client to stand by for the data transmission, the communication control unit 504 transmits the second control information to the second client by using the communicator 405 (S1211). The first control information indicates an instruction to stop the data transmission via the access point to which the first client is being connected. The second control information indicates an instruction to stand by for the data transmission via the access point to which the second client is being connected.

The server in each aspect of the present invention need not have a configuration corresponding to at least one of the display unit 401, the input unit 402, and the recording unit 404. The server in each aspect of the present invention need not have a configuration corresponding to at least one of the STA information management unit 501 and the analysis processing unit 503.

The communicator 405 may receive the surrounding AP information from the STA (client) before the reception of the data is started. The surrounding AP information indicates an access point, to which the STA is not being connected, which is present in surroundings of the STA. In a case in which the first condition is satisfied and the surrounding AP information has been received, the communication control unit 504 may transmit connection instruction information to the second client by using the communicator 405. The connection instruction information indicates an instruction to connect to the access point indicated by the surrounding AP information.

As described above, the STA (client) is one of the first client and the second client. The decision processing is processing for deciding which of the first state and the second state to be set. The first state is a state in which the first client performs data transmission. The second state is a state in which the second client performs data transmission. The STA has the communicator (the communicator 601, the communicator 605) and the communication control unit 704.

The communicator 605 receives data at an application level from an external terminal (S1402). The communicator 601 transmits the data received from the external terminal to the WS 101 (S1705). The communicator 601 transmits connection AP information, priority information, and surrounding AP information to the WS 101 before transmission of the data is started (S1411) and receives one of first control information, second control information, and connection instruction information from the WS 101 (S1412, S1701). In a case in which the first control information has been received, the communication control unit 704 stops the data transmission via the access point to which the first client is being connected (S1707). In a case in which the second control information has been received, the communication control unit 704 stands by for the data transmission via the access point to which the second client is being connected (S1414). In a case in which the connection instruction information has been received, the communication control unit 704 connects to the access point indicated by the surrounding AP information by using the communicator 601 (S1505).

The client according to each aspect of the present invention need not have a configuration corresponding to at least one of the input unit 602, the recording unit 604, and the battery 606. The client according to each aspect of the present invention need not have a configuration corresponding to at least one of the information management unit 701, the examination data processing unit 702, the system control unit 703, and the state control unit 705.

The communication system according to the embodiment of the present invention has a WS 101 (server) and an STA (client). The WS 101 has the communicator 405 (first communicator), the decision unit 502 (decider), and the communication control unit 504 (communication controller, first communication controller). The STA has the communicator (the communicator 601, the communicator 605) (second communicator) and the communication control unit 704 (communication controller, second communication controller).

The communication system according to each aspect of the present invention need not have a configuration corresponding to the access point.

A communication method performed by the WS 101 has a first step, a second step, a third step, and a fourth step. The WS 101 receives data at an application level from the STA (client) in the first step (S1103). The WS 101 receives the connection AP information and the priority information from the STA in the second step (S1101) before the reception of the data is started. The WS 101 determines whether or not the first condition is satisfied (S1201) and determines whether or not any one of the second condition and the third condition is satisfied (S1206, S1205) in the decision processing (S1102) in the third step. In a case in which the first condition and the second condition are satisfied, the WS 101 decides to cause the first client to stop the data transmission in the decision processing in the third step (S1207). In a case in which the first condition and the third condition are satisfied, the WS 101 decides to cause the second client to stand by for the data transmission in the decision processing in the third step (S1210). In a case in which decision to cause the first client to stop the data transmission has been made in the third step, the WS 101 transmits the first control information to the first client in the fourth step (S1207). In a case in which the decision to cause the second client to stand by for the data transmission has been made in the third step, the WS 101 transmits the second control information to the second client in the fourth step (S1211).

The communication method performed by the server according to each aspect of the present invention need not have steps other than the aforementioned first step, second step, third step, and fourth step.

A program may cause a computer of the WS 101 (server) to execute the aforementioned first step, second step, third step, and fourth step.

The communication method performed by the STA has a first step, a second step, a third step, a fourth step, and a fifth step. The STA receives data at an application level from an external terminal in the first step (S1402). The STA transmits the data received from the external terminal to the WS 101 (server) in the second step (S1705). The STA transmits connection AP information, priority information, and surrounding AP information to the WS 101 in the third step (S1411) before transmission of the data is started. The STA receives one of first control information, second control information, and connection instruction information from the WS 101 in the fourth step (S1412, S1701). In a case in which the first control information has been received, the STA stops the data transmission via the access point to which the first client is being connected in the fifth step (S1707). In a case in which the second control information has been received, the STA stands by for the data transmission via the access point to which the second client is being connected in the fifth step (S1414). In a case in which the connection instruction information has been received, the STA connects to the access point indicated by the surrounding AP information in the fifth step (S1505).

The communication method performed by the client according to each aspect of the present invention need not have steps other than the aforementioned first step, second step, third step, fourth step, and fifth step.

The program may cause a computer of the STA (client) to execute the aforementioned first step, second step, third step, fourth step, and fifth step.

In the embodiment of the present invention, a state of data transmission is decided in accordance with a priority of each STA in a case in which a plurality of STAs are connected to one access point. Alternatively, in a case which a plurality of STAs are connected to one access point, the STA connects to an access point that is different from the access point to which the plurality of STAs are being connected before the STA performs data transmission. Therefore, it is possible to reduce occurrence of congestion. In addition, an STA with high priority can perform data transmission. In the embodiment of the present invention, it is not necessary to replace existing access points or to change setting.

In a case in which the decision unit 502 decides to cause the first client to stop the data transmission, the communication control unit 504 may transmit clock time information to the first client by using the communicator 405 (S1207). In a case in which the decision unit 502 decides to cause the second client to stand by for the data transmission, the communication control unit 504 may transmit clock time information to the second client by using the communicator 405 (S1211). The clock time information indicates a clock time when the data transmission via the access point to which the first client or the second client is being connected may be started.

The communicator 601 may receive the clock time information from the WS 101 (server) (S1412, S1701). In a case in which one of the first control information and the second control information has been received and the clock time information has been received, the communication control unit 704 may start the data transmission via the access point to which the first client or the second client is being connected at the clock time indicated by the clock time information (S1503, S1705).

After the STA stops the data transmission or after the STA stands by for the data transmission, the STA starts the data transmission at the clock time indicated by the clock time information. Therefore, occurrence of congestion is reduced.

The communicator 405 may receive data amount information from the STA (client) before the reception of the data is started (S1101). The data amount information indicates the amount of data that is scheduled to be transmitted to the WS 101 (server). In a case in which the decision unit 502 decides to cause the first client to stop the data transmission, the decision unit 502 may calculate the clock time when the data transmission may be started on the basis of a first data amount and a second data amount (S1207). The first data amount is the amount of data indicated by the data amount information received from the first client. The second data amount is the amount of data that has already been received from the first client. In a case in which the decision unit 502 decides to cause the second client to stand by for the data transmission, the decision unit 502 may calculate the clock time when the data transmission may be started on the basis of the amount of data indicated by the data amount information received front the second client (S1210).

The communicator 601 may transmit the data amount information to the WS 101 (server) before transmission of the data is started (S1411).

The clock time when the data transmission may be started is calculated on the basis of the amount of the data that has not yet been transmitted. Therefore, it is possible for the STA to start the data transmission such that occurrence of congestion is reduced.

The data may be examination data acquired by the examination terminal that performs examination of the inside of a body. The priority information may be at least one of position information, abnormality information, and operation information. The position information indicates the position of the examination terminal in the body. The abnormality information indicates a degree of abnormality of the inside of the body estimated from the examination data. The operation information indicates occurrence of a predetermined operation by the user.

The examination data processing unit 702 may generate the position information and the abnormality information on the basis of the examination data (1409).

The priority information includes highly urgent information. Therefore, as highly urgent STA can perform data transmission, and congestion is reduced.

The decision unit 502 may determine whether or not the data transmission by the STA (transmitting client) ends within a predetermined time on the basis of the data transmission ability (data transmission speed) of the STA after one of the first control information and the second control information is transmitted (S1304). In a case in which the first control information is transmitted, the STA is the second client. In a case in which the second control information is transmitted, the STA is the first client. In a case in which the data transmission by the STA does not end within the predetermined time, the decision unit 502 may decide to cause the STA to stop the data transmission (S1305). In a case in which the decision unit 502 decides to cause the STA to stop the data transmission the communicator 405 may transmit third control information to the STA by using the communicator 405 (S1305). The third control information indicates an instruction to stop the data transmission via the access point to which the STA is being connected.

In a case in which the third control information has been received, the communication control unit 704 may stop the data transmission via the access point to which the STA (client) is being connected (S1707).

An increase in communication traffic leads to a decrease in throughput. The decrease in throughput leads to a long communication time. In a case in which the data transmission does not end within the predetermined time, an increase in power consumption of the STA due to the data transmission is avoided by the STA stopping the data transmission.

In a case in which the battery remaining amount of the STA (client) is less than the predetermined amount, the system control unit 703 may reduce the amount of the data to be transmitted to the WS 101 (server) (S1704). The communication control unit 704 may transmit the data, the amount of which has been reduced to the WS 101 by using the communicator 601 (S1705).

An increase in power consumption of the STA due to the data transmission is avoided by the amount of data being reduced in a case in which the battery remaining amount of the STA is less than the predetermined amount. Therefore, the data transmission is easily completed before it becomes impossible for the STA to perform the data transmission due to the decrease in the battery remaining amount.

The communicator may include the communicator 605 (first communicator) that communicates with an external terminal and the communicator 601 (second communicator) that communicates with the WS 101 (server). In a case in which the battery remaining amount of the STA (client) is less than the predetermined amount, the state control unit 705 may bring only the communicator 601 into the resting state (S1602).

In a case in which the battery remaining amount of the STA is less than the predetermined amount, the STA can continue the communication with the external terminal by causing only the communicator 601 to rest.

While preferred embodiments of the invention have been described and shown above, it should be understood that these are exemplars of the invention and are not to be considered as limiting. Additions, omissions, substitutions, and other modifications can be made without departing, from the spirit or scope of the present invention. Accordingly, the invention is not to be considered as being limited by the foregoing description, and is only limited by the scope of the appended claims.

What is claimed is:

1. A server comprising:
 a processor that is configured to include
  a communicator that is configured to receive data at an application level from a client and receive connection AP information and priority information from the client before reception of the data is started, the client being one of a first client and a second client, the first client being a terminal that has already started data transmission to the server at a timing when a decision processing is started, the second client being a terminal that is standing by for the data transmission to the server at the timing when the decision processing is started, the connection AP information indicating an access point to which the client is being connected, the priority information indicating a priority of the client;
  a decision unit that is configured to determine whether or not a first condition is satisfied and determine whether or not any one of a second condition and a third condition is satisfied in the decision processing, and decide to cause the first client to stop the data transmission in the decision processing in a case in which the first condition and the second condition are satisfied, or decide to cause the second client to stand by for the data transmission in the decision processing in a case in which the first condition and the third condition are satisfied, the first condition indicating that an access point indicated by the connection AP information received from the first client is the same as an access point indicated by the connection AP information received from the second client, the second condition indicating that a priority indicated by the priority information received from the first client is lower than a priority indicated by the priority information received from the second client, the third condition indicating that the priority information has not been received from the second client; and
  a communication control unit that is configured to transmit first control information to the first client by using the communicator in a case in which the decision unit decides to cause the first client to stop the data transmission and transmit second control information to the second client by using the communicator in a case in which the decision unit decides to cause the second client to stand by for the data transmission, the first control information indicating an instruction to stop data transmission via an access point to which the first client is being connected, the second control information indicating an instruction to stand by for data transmission via an access point to which the second client is being connected,
 wherein the decision processing decides to stop or start the transmission based on the conditions.

2. The server according to claim 1,
wherein the communicator is further configured to receive surrounding AP information from the client before the reception of the data is started, the surrounding AP information indicating an access point, to which the client is not being connected, which is present in surroundings of the client, and
the communication control unit is further configured to transmit connection instruction information to the second client by using the communicator in a case in which the first condition is satisfied and the surrounding AP information has been received, the connection instruction information indicating an instruction to connect to the access point indicated by the surrounding AP information.

3. The server according to claim 1,
wherein the communication control unit is further configured to transmit clock time information to the first client by using the communicator in a case in which the decision unit decides to cause the first client to stop the data transmission,
the communication control unit is further configured to transmit the clock time information to the second client by using the communicator in a case in which the decision unit decides to cause the second client to stand by for the data transmission.

4. The server according to claim 3,
wherein the communicator is further configured to receive data amount information from the client before the reception of the data is started, the data amount information indicating the amount of data that is scheduled to be transmitted to the server,
the decision unit is configured to calculate the clock time on the basis of a first data amount and a second data amount in a case in which the decision unit decides to cause the first client to stop the data transmission, the first data amount being the amount of data indicated by the data amount information received from the first client, the second data amount being the amount of data that has already been received from the first client, and
the decision unit is configured to calculate the clock time on the basis of the amount of data indicated by the data amount information received from the second client in a case in which the decision unit decides to cause the second client to stand by for the data transmission.

5. The server according to claim 1,
wherein the data is examination data that is acquired by an examination terminal for examining the inside of a body, and
the priority information is at least one of position information, abnormality information, and operation information, the position information indicating a position of the examination terminal in the body, the abnormality information indicating a degree of abnormality of an inside of the body estimated from the examination data, the operation information indicating occurrence of a predetermined operation by a user.

6. The server according to claim 1,
wherein the decision unit is further configured to determine whether or not data transmission by a transmitting client will end within a predetermined time on the basis of a data transmission ability of the transmitting client after one of the first control information and the second control information is transmitted, the transmitting client being the second client in a case in which the first control information is transmitted, the transmitting client being the first client in a case in which the second control information is transmitted,
the decision unit is further configured to decide to cause the transmitting client to stop the data transmission in a case in which the data transmission by the transmitting client will not end within the predetermined time, and
the communication control unit is further configured to transmit third control information to the transmitting client by using the communicator in a case in which the decision unit decides to cause the transmitting client to stop the data transmission, the third control information indicating an instruction to stop data transmission via an access point to which the transmitting client is being connected.

7. A communication system, comprising:
a server; and
a client,
wherein the server includes a processor that is configured to include
a first communicator that is configured to receive data at an application level from the client and receive connection AP information and priority information from the client before reception of the data is started, the client being one of a first client and a second client, the first client being a terminal that has already started data transmission to the server at a timing when a decision processing is started, the second client being a terminal that is standing by for the data transmission to the server at the timing when the decision processing is started, the connection AP information indicating an access point to which the client is being connected, the priority information indicating a priority of the client,
a decision unit that is configured to determine whether or not a first condition is satisfied and determine whether or not any one of a second condition and a third condition is satisfied in the decision processing, and decide to cause the first client to stop the data transmission in the decision processing in a case in which the first condition and the second condition are satisfied, or decide to cause the second client to stand by for the data transmission in the decision processing in a case in which the first condition and the third condition are satisfied, the first condition indicating that an access point indicated by the connection AP information received from the first client is the same as an access point indicated by the connection AP information received from the second client, the second condition indicating that a priority indicated by the priority information received from the first client is lower than a priority indicated by the priority information received from the second client, the third condition indicating that the priority information has not been received from the second client, and
a first communication control unit that is configured to transmit first control information to the first client by using the first communicator in a case in which the decision unit decides to cause the first client to stop the data transmission, or transmit second control information to the second client by using the first communicator in a case in which the decision unit decides to cause the second client to stand by for the data transmission, the first control information indicating an instruction to stop data transmission via an access point to which the first client is being connected, the second control information indicating an instruction to stand by for the data transmission via an access point to which the second client is being connected, and
the client includes
a second communicator that is configured to receive the data from an external terminal, transmit the data received from the external terminal to the server, transmit the connection AP information and the priority information to the server before transmission of the data is started, and receive one of the first control information and the second control information from the server, and
a second communication control unit that is configured to stop the data transmission via the access point to which the first client is being connected in a case in which the first control information has been received or stand by for the data transmission via the access point to which the second client is being connected in a case in which the second control information has been received,
wherein the decision processing decides to stop or start the transmission based on the conditions.

8. A communication method that is performed by a server, the method comprising:
a first step in which the server receives data at an application level from a client, the client being one of a first client and a second client, the first client being a terminal that has already started data transmission to the server at a timing when a decision processing is started, the second client being a terminal that is standing by for the data transmission to the server at the timing when the decision processing is started;
a second step in which the server receives connection AP information and priority information from the client before reception of the data is started, the connection AP information indicating an access point to which the client is being connected, the priority information indicating a priority of the client;

a third step in which the server determines whether or not a first condition is satisfied and determines whether or not any one of a second condition and a third condition is satisfied in the decision processing, and the server decides to cause the first client to stop the data transmission in the decision processing in a case in which the first condition and the second condition are satisfied, or the server decides to cause the second client to stand by for the data transmission in the decision processing in a case in which the first condition and the third condition are satisfied, the first condition indicating that an access point indicated by the connection AP information received from the first client is the same as an access point indicated by the connection AP information received from the second client, the second condition indicating that a priority indicated by the priority information received from the first client is lower than a priority indicated by the priority information received from the second client, the third condition indicating that the priority information has not been received from the second client; and a fourth step in which the server transmits first control information to the first client in a case in which the server decides to cause the first client to stop the data transmission in the third step or the server transmits second control information to the second client in a case in which the server decides to cause the second client to stand by for the data transmission in the third step, the first control information indicating an instruction to stop data transmission via an access point to which the first client is being connected, and the second control information indicating an instruction to stand by for data transmission via an access point to which the second client is being connected, wherein the decision processing decides to stop or start the transmission based on the conditions.

9. A non-transitory computer-readable recording medium that records a program for causing a computer of a server to execute a first step, a second step, a third step, and a fourth step, wherein the server receives data at an application level from a client in the first step, the client being one of a first client and a second client, the first client being a terminal that has already started data transmission to the server at a timing when decision processing is started, the second client being a terminal that is standing by for the data transmission to the server at the timing when the decision processing is started, the server receives connection AP information and priority information from the client in the second step before reception of the data is started, the connection AP information indicating an access point to which the client is being connected, the priority information indicating a priority of the client, the server determines whether or not a first condition is satisfied and determines whether or not any one of a second condition and a third condition is satisfied in the decision processing in the third step, and the server decides to cause the first client to stop the data transmission in the decision processing in the third step in a case in which the first condition and the second condition are satisfied, or the server decides to cause the second client to stand by for the data transmission in the decision processing in the third step in a case in which the first condition and the third condition are satisfied, the first condition indicating that an access point indicated by the connection AP information received from the first client is the same as an access point indicated by the connection AP information received from the second client, the second condition indicating that a priority indicated by the priority information received from the first client is lower than a priority indicated by the priority information received from the second client, the third condition indicating that the priority information has not been received from the second client, the server transmits first control information to the first client in the fourth step in a case in which the server decides to cause the first client to stop the data transmission in the third step, or the server transmits second control information to the second client in the fourth step in a case in which the server decides to cause the second client to stand by for the data transmission in the third step, the first control information indicating an instruction to stop data transmission via an access point to which the first client is being connected, the second control information indicating an instruction to stand by for data transmission via an access point to which the second client is being connected, wherein the decision processing decides to stop or start the transmission based on the conditions.

* * * * *